(12) United States Patent
Gerard et al.

(10) Patent No.: US 11,040,095 B2
(45) Date of Patent: Jun. 22, 2021

(54) HUMAN RHINOVIRUS VACCINE

(71) Applicant: GLAXOSMITHKLINE BIOLOGICALS, S.A., Rixensart (BE)

(72) Inventors: Catherine Marie Ghislaine Gerard, Rixensart (BE); Sandra Giannini, Rixensart (BE); Julien Thierry Massaux, Rixensart (BE)

(73) Assignee: GlaxoSmithKline Biologicals S.A., Rixensart (BE)

( * ) Notice: Subject to any disclaimer, the term of this patent is extended or adjusted under 35 U.S.C. 154(b) by 0 days.

(21) Appl. No.: 16/338,821

(22) PCT Filed: Oct. 5, 2017

(86) PCT No.: PCT/IB2017/056147
§ 371 (c)(1),
(2) Date: Apr. 2, 2019

(87) PCT Pub. No.: WO2018/065931
PCT Pub. Date: Apr. 12, 2018

(65) Prior Publication Data
US 2019/0224303 A1    Jul. 25, 2019

(30) Foreign Application Priority Data
Oct. 5, 2016 (GB) .................................. 1616904

(51) Int. Cl.
| | |
|---|---|
| *A61K 39/125* | (2006.01) |
| *A61K 39/00* | (2006.01) |
| *A61K 39/12* | (2006.01) |
| *C07K 14/005* | (2006.01) |
| *A61P 31/16* | (2006.01) |
| *A61K 39/39* | (2006.01) |

(52) U.S. Cl.
CPC .............. *A61K 39/12* (2013.01); *A61K 39/39* (2013.01); *A61P 31/16* (2018.01); *C07K 14/005* (2013.01); *A61K 2039/55555* (2013.01); *A61K 2039/55577* (2013.01); *A61K 2039/55583* (2013.01); *C07K 2319/00* (2013.01); *C12N 2770/32722* (2013.01); *C12N 2770/32734* (2013.01)

(58) Field of Classification Search
None
See application file for complete search history.

(56) References Cited

U.S. PATENT DOCUMENTS

| | | | | |
|---|---|---|---|---|
| 5,714,374 | A * | 2/1998 | Arnold | C12N 15/86 424/93.6 |
| 2006/0210555 | A1* | 9/2006 | Kensil | A61P 25/28 424/133.1 |
| 2016/0022803 | A1* | 1/2016 | Baudoux | C12N 7/00 424/450 |

FOREIGN PATENT DOCUMENTS

| | | | | |
|---|---|---|---|---|
| WO | WO-2014145174 | A1 * | 9/2014 | C07K 14/005 |
| WO | WO-2016042059 | A1 * | 3/2016 | A61K 39/12 |

OTHER PUBLICATIONS

Glanville et al., "Challenges in developing a cross-serotype rhinovirus vaccine," Current Opinion in Virology, 11:83-88 (Year: 2015).*

(Continued)

*Primary Examiner* — M Franco G Salvoza
(74) *Attorney, Agent, or Firm* — Dana L. Broughton

(57) ABSTRACT

HRV VP2 proteins useful as components of immunogenic compositions for the induction of cross-reactive cell-mediated immunity against human rhinovirus infection; nucleic acid constructs encoding such HRV VP2 proteins.

Figure 1:
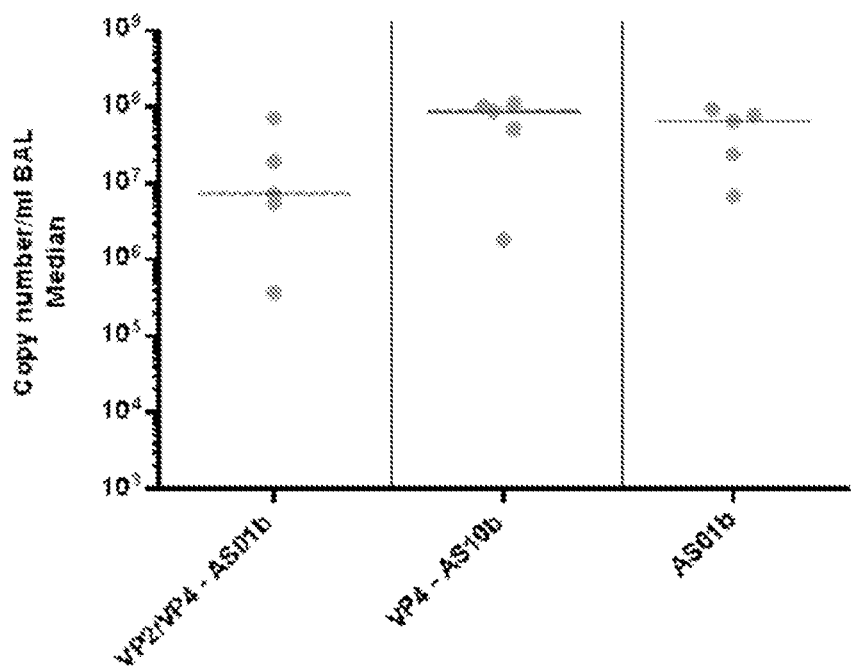

15 Claims, 12 Drawing Sheets
Specification includes a Sequence Listing.

(56) References Cited

OTHER PUBLICATIONS

Greenberg, "Update on Human Rhinovirus and Coronavirus Infections," Semin Respir Crit Care Med 37:555-571 (Year: 2016).*

Hastings et al., "Neutralizing antibodies to human rhinovirus produced in laboratory animals and humans that recognize a linear sequence from VP2," Journal of General Virology, 71: 3055-3059 (Year: 1998).*

Briuglia et al., "Influence of cholesterol on liposome stability and on in vitro drug release," Drug Deliv and Transl. Res: 231-242 (Year: 2015).*

* cited by examiner

Figure 16B

Percent amino acid identity across select VP2 protein sequences

|         | HRV_39 | HRV_89 | HRV_1B | HRV_02 | HRV_14 |
|---------|--------|--------|--------|--------|--------|
| HRV_39  | 100%   | 75.5%  | 85.2%  | 77.5%  | 62.1%  |
| HRV_89  | 75.5%  | 100%   | 76.9%  | 74.8%  | 61.5%  |
| HRV_1B  | 85.2%  | 76.9%  | 100%   | 76.7%  | 61.0%  |
| HRV_02  | 77.5%  | 74.8%  | 76.7%  | 100%   | 61.1%  |
| HRV_14  | 62.1%  | 61.5%  | 61.0%  | 61.1%  | 100%   |

Figure 16C

```
              1         10        20        30        40        50        60
              |         |         |         |         |         |         |
HRV_39 - VP2  SPTVEACGYSDRIIQITRGDSTITSQDVANAVVGYGVWPHYLTADDASAIDRPTQPDTSS
HRV_89 - VP2  SPTVEACGYSDRLIQITRGDSTITSQDTANAVVAYGVWPSYLTPDDATAIDRPTQPDTSS
HRV_1B - VP2  SPSVEACGYSDRIIQITRGDSTITSQDVANAVVGYGVWPHYLTPQDATAIDRPTQPDTSS
HRV_02 - VP2  SPTVEACGYSDRIIQITRGDSTITSQDVANAIVAYGVWPHYLSSKDASAIDRPSQPDTSS
HRV_14 - VP2  SPNVEACGYSDRVQQITLGNSTITTQEAANAVVCYAEWPEYLPDVDASDVNKTSKPDTSV

HRV_39 - VP2  NRFYTLESKVWKRDSRGWWWKLPDALKDMGIFGENMYYHFLGRSGYTVHVQCNASKFHQG
HRV_89 - VP2  NRFYTLDSRSWTSASSGWWWKLPDALKNMGIFGENMFYHFLGRSGYTIHVQCNSSKFHQG
HRV_1B - VP2  NRFYTLESKHWNGDSRGWWWKLPDALKEMGIFGENMYYHFLGRSGYTVHVQCNASKFHQG
HRV_02 - VP2  NRFYTLRSVTWSSSSRGWWWKLPDALKDMGIFGENMFYHYLGRSGYTIHVQCNASKFHQG
HRV_14 - VP2  CRFYTLDSRTWTTGSRGWCWKLPDALKDMGVFGQNMFFHSLGRSGYTVHVQCNATKFHSG

HRV_39 - VP2  TLLIAMVPEHQLASANYGNVTAGYNYTHPGEAGRDV-GQQRTNNERQPSDDNWLNFDGTL
HRV_89 - VP2  LLIVAAIPEHQLASATSGNVSVGYNHTHPGEQGREVVPSRTSSDNKRPSDDSWLNFDGTL
HRV_1B - VP2  TLLVAMIPEHQLASAKNGSVTAGYNLTHPGEAGR-VVSGQRDANLRQPSDDSWLNFDGTL
HRV_02 - VP2  TLIVALIPEHQIASALHGNVNVGYNYTHPGETGREVKAEIRLNPDLQPTEEYWLNFDGTL
HRV_14 - VP2  CLLVVVIPEHQLASHEGGNVSVKYIFFHPGERGIDL---SSANEVGGPVKDVIYNMNGTL

HRV_39 - VP2  LGNLLIFPHQFINLRSNNSATIIVPYVNAVPMDSMLRHNNWSLLIIPVSPLEADTSATAI
HRV_89 - VP2  LGNLPIYPHQYINLRTNNSATLILPYVNAVPMDSMLRHNNWSLVIIPICPLQVQPGGTQS
HRV_1B - VP2  LGNLLIFPHQFINLRSNNSATLIVPYVNAVPMDSMLRHNNWSLVIIPISPLRSETTSSNI
HRV_02 - VP2  LGNITIFPHQFINLRSNNSATIIAPYVNAVPMDSMRSHNNWSLVIIPICPLET-SSAINT
HRV_14 - VP2  LGNLLIFPHQFINLRTNNTATIVIPYINSVPIDSMIRHNNVSLMVIPIAPLTVPTGATPS

HRV_39 - VP2  VPITVSISPMFSEFSGARARPAAAI--
HRV_89 - VP2  IPITVSISPMFSEFSGPRSKVVFSTTQ
HRV_1B - VP2  RPITVSISPMCAEFSGARAKNVRQ---
HRV_02 - VP2  IPITISISPMCAEFSGARAKRQ-----
HRV_14 - VP2  LPITVIAPMCTEFSGIRSKSIVPQ--
```

HUMAN RHINOVIRUS VACCINE

BACKGROUND

The present invention relates to immunogenic compositions for use in the prevention or amelioration of disease caused by human rhinovirus.

Human Rhinoviruses (HRVs) are the most common viral infective agents in humans and are the predominant cause of the common cold. HRVs are also linked to exacerbations of chronic obstructive pulmonary disease (COPD), asthma development, and, more recently, severe bronchiolitis in infants and children as well as fatal pneumonia in elderly and immunocompromised adults. Consequently, HRV vaccine development is highly recommended but efforts are hindered by the existence of more than 100 HRV serotypes, with high-level sequence variability in the antigenic sites. Humoral immune responses are important for preventing HRV infection. HRV infection in antibody-naïve subjects is followed by the development of serotype-specific neutralizing serum antibodies (IgG) as well as secretory antibodies (IgA) in the airways. Human challenge studies have demonstrated that pre-existing HRV type specific antibodies can protect against HRV infection (Alper et al, 1998). CD4-specific cell responses develop as consequences of HRV infection. CD4 cells are largely Th1-like and their production of IFN-γ contributes to the anti-viral immune response, but these CD4 cells could also facilitate development of the humoral immune response.

Figure 9:
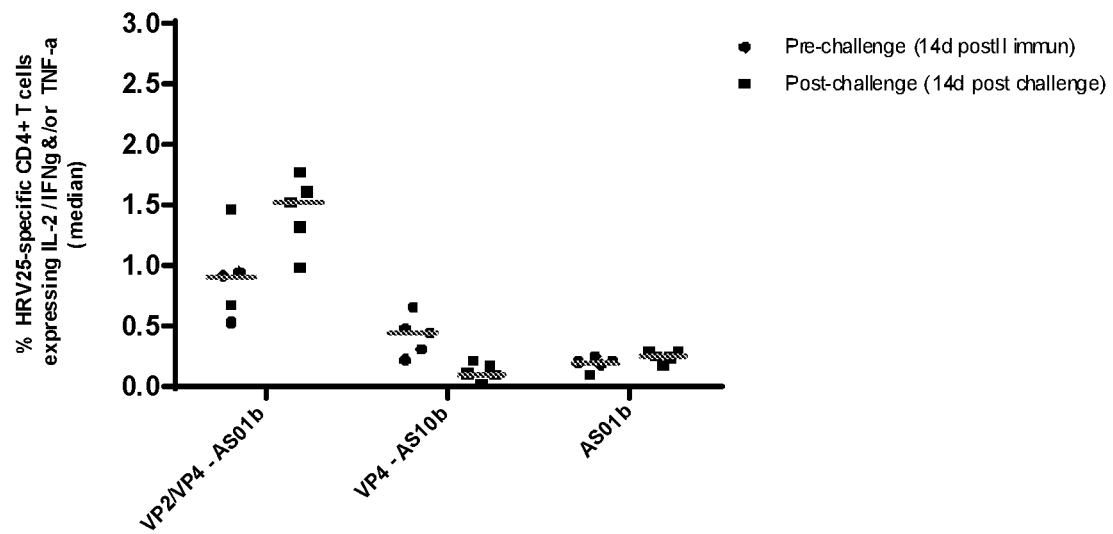

Literature indicates that priming with IFA-adjuvanted HRV16 VP0 protein directly impacted the magnitude of heterotypic neutralizing antibodies induced to rhinovirus infection (Glanville et Al. 2013). In WO 2014/122220, based on the Glanville results, the VP4 protein was identified as having high homology across HRVs, and therefore held responsible for VP0 induced cross-reactive helper CD4-T cells which could accelerate the generation of neutralizing antibodies upon natural HRV infections. In WO 2016/134288, CD4+ T cell peptide epitopes were identified.

SUMMARY

Provided herein are HRV VP2 proteins useful as components of immunogenic compositions for the induction of broadly cross-reactive cell-mediated immunity against Rhinovirus infection.

In some embodiments, an immunogenic composition is provided comprising a HRV VP2 protein, in particular in combination with an adjuvant, e.g. a Th1 adjuvant, such as a saponin-containing adjuvant.

In some embodiments, a nucleic acid sequence encoding a polypeptide comprising a HRV VP2 protein is provided. In some embodiments, a vector comprising such a nucleic acid sequence encoding a polypeptide comprising a HRV VP2 protein is provided, such as an adenoviral vector. In some embodiments, a self-amplifying RNA molecule comprising the nucleic acid sequence encoding a polypeptide comprising a HRV VP2 protein is provided, such as an SAM vector. In further embodiments, immunogenic compositions comprising such vectors or nucleic acid sequences are provided.

In some embodiments, such immunogenic compositions comprising HRV VP2 protein in combination with an adjuvant, and/or, nucleic acid based constructs encoding HRV VP2 proteins, are provided for use in medicine, e.g. for use in the prevention or amelioration of disease or disease symptoms caused by or associated with HRV infection in a subject, or, for use in a subject to reduce recovery time from and/or lower disease severity caused by HRV infection of a subject, or, for use in a subject to reduce or prevent the clinical symptoms upon HRV infection of the subject, or, for use in a subject to induce a cross-reactive immune response against at least three serotypes of HRV, such as wherein at least one of the at least three serotypes of HRV belongs to type A HRV and at least one other of the at least three serotypes of HRV belongs to type B HRV or type C HRV.

In some embodiments, the immunogenic composition is for use in subjects having COPD (such as elderly people) or asthma (such as infants or children).

In some embodiments, methods for reducing recovery time from and/or lowering disease severity caused by HRV infection in a subject in need thereof, which comprises administering to said subject an immunologically effective amount of an immunogenic composition as disclosed herein.

In some embodiments, methods for reducing or preventing the clinical symptoms upon HRV infection in a subject in need thereof, which comprises administering to said subject an immunologically effective amount of an immunogenic composition as disclosed herein.

In some embodiments, methods for inducing a cross-reactive immune response against at least three serotypes of HRV in a subject in need thereof, which comprises administering to said subject an immunologically effective amount of an immunogenic composition as disclosed herein.

BRIEF DESCRIPTION OF THE FIGURES

FIG. 1: Quantification of single stranded positive RNA genome in BAL fluids at D2 post intranasal HRV1b challenge—each dot represents individual values of a mouse (n=5/group) and results are shown with the median (horizontal lines).

FIG. 2: White blood cells (lymphocytes, neutrophils, macrophages, eosinophils) differential counts in BAL fluids collected 2 days post-HRV1b challenge. Each dot represents individual values of a mouse (n=5/group) and results are shown with the median (horizontal lines).

FIG. 3: The levels of inflammatory cytokines (TNF-α, INF-γ, IL-6, IL-10 & IL-12p70) & chemokines (MCP-1) secreted in BAL fluids were investigated 2 days post-HRV1b challenge. Each dot represents individual values of a mouse (n=5/group) and results are shown with the median (horizontal lines).

FIG. 4: Specific CD4+T cell response following in-vitro stimulation with HRV39 VP2 peptides. The data are shown for individual mice (dots; n=5/group) with the median/group (horizontal line).

FIG. 5: Specific CD4+T cell response following in-vitro stimulation with HRV2 VP4 peptides. The data are shown for individual mice (dots; n=5/group) with the median/group (horizontal line).

FIG. 6: Specific CD4+T cell response following in-vitro stimulation with HRV39 VP4 peptides. The data are shown for individual mice (dots; n=5/group) with the median/group (horizontal line).

FIG. 7: Specific CD4+T cell response following in-vitro stimulation with HRV2 VP2 peptides. The data are shown for individual mice (dots; n=5/group) with the median/group (horizontal line).

FIG. 8: Specific CD4+T cell response following in-vitro stimulation with HRV14 VP2 peptides. The data are shown for individual mice (dots; n=5/group) with the median/group (horizontal line).

FIG. 9: Specific CD4+T cell response following in-vitro stimulation with UC HRV25 particles. The data are shown for individual mice (dots; n=5/group) with the median/group (horizontal line).

Figure 10:
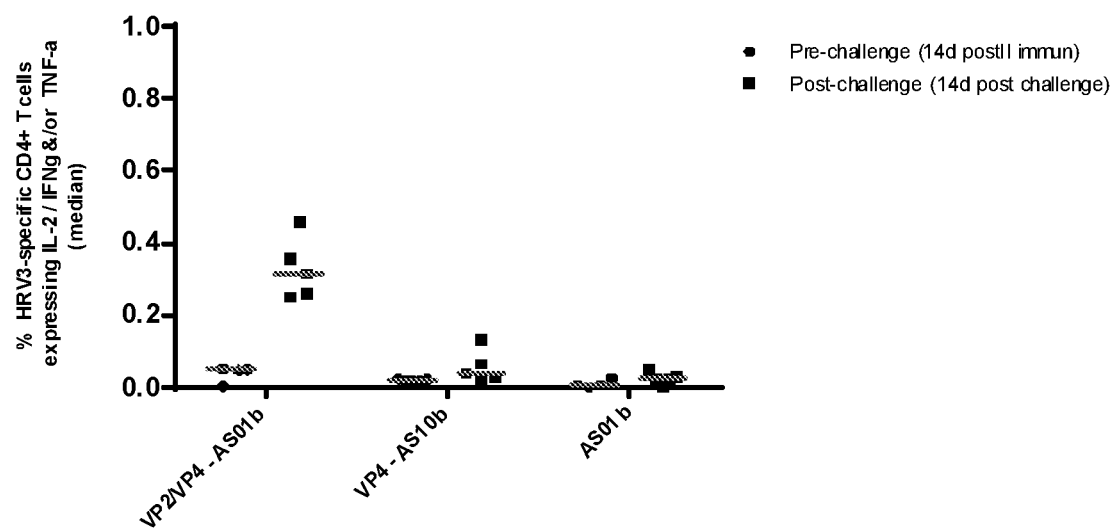

FIG. 10: Specific CD4+T cell response following in-vitro stimulation with UC HRV3 peptides. The data are shown for individual mice (dots; n=5/group) with the median/group (horizontal line).

Figure 11:
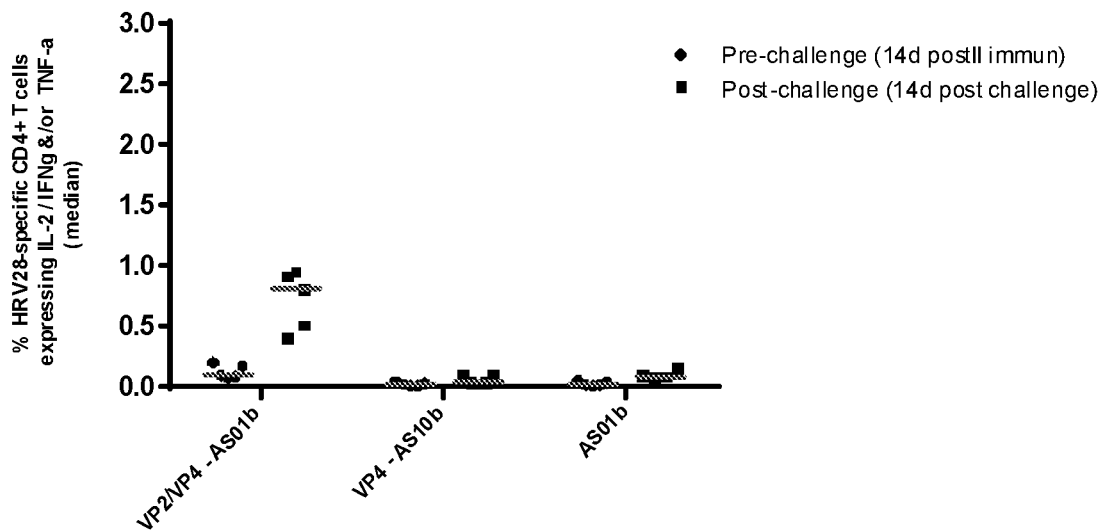

FIG. 11: Specific CD4+T cell response following in-vitro stimulation with UC HRV28 particles. The data are shown for individual mice (dots; n=5/group) with the median/group (horizontal line).

Figure 12:
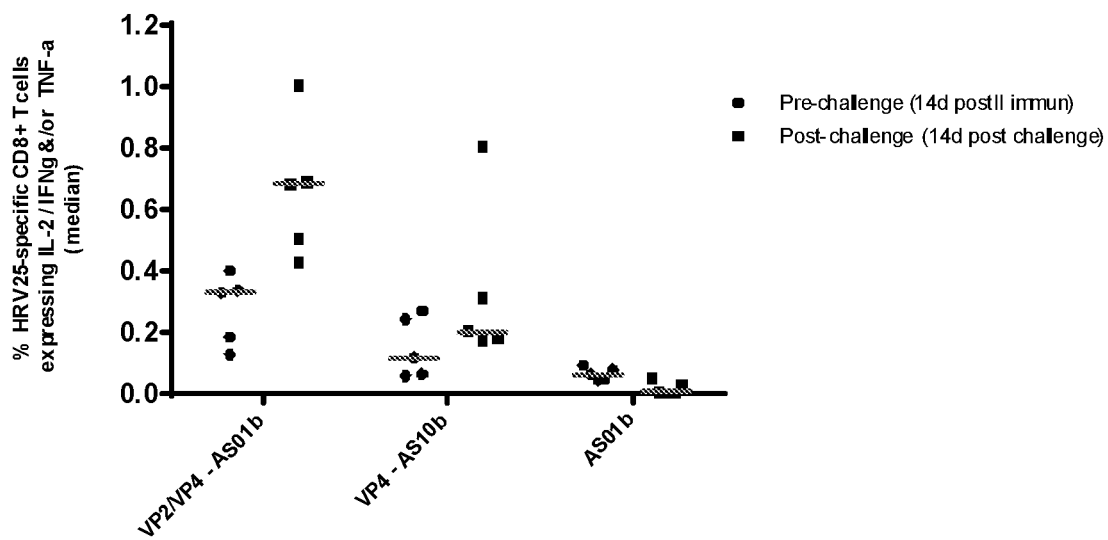

FIG. 12: Specific CD8+T cell response following in-vitro stimulation with UC HRV25 particles. The data are shown for individual mice (dots; n=5/group) with the median/group (horizontal line).

Figure 13:
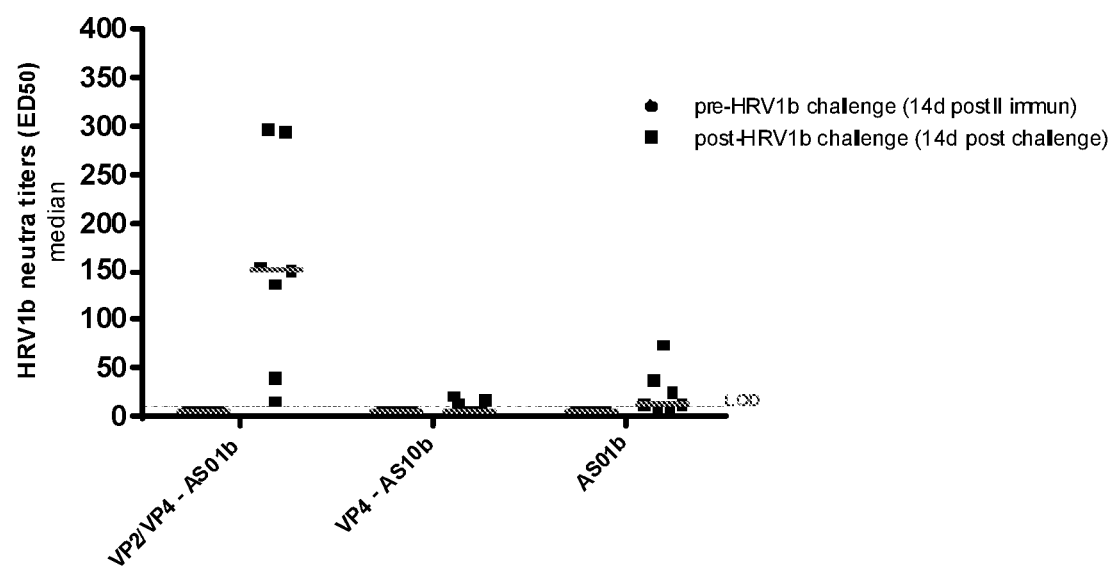

FIG. 13: HRV1b-specific neutralizing antibody response detected pre/post HRV1b challenge. The data are shown for pooled mice sera (5 or 7 pools of 3 mice/group) with the median/group (horizontal line).

FIG. 14: IFN-γ production by CD4+ CD44+ T-cells in mice immunized with HRV39 VP2, VP4 or VP0; IFN-γ was elicited in HRV39 VP2 and VP0 immunized mice in response to peptide pools generated from VP2 of homologous (14A) or heterologous (14B, 14C, 14D, or 14E) HRV viruses. Data displayed are individual mice (n=6 per group) with the median indicated with a horizontal line. Moving from left to right in each Figure, the columns show data from mice immunized with HRV39 VP2, HRV39 VP4, HRV39 VP0, HRV39 live virus, and saline, respectively. Note differences in upper limit on Y-axis.

FIG. 15: IFN-γ production by CD4+ CD44+ T-cells from mice immunized with HRV39 VP2, VP4 or VP0: little to no IFN was produced in response to peptide pools generated from VP4 of homologous (15A) or heterologous (15B, 15C, 15D, 15E) HRV types. Data displayed are individual mice (n=6 per group) with the median indicated with a horizontal line. Moving from left to right in each Figure, the columns show data from mice immunized with HRV39 VP2, HRV39 VP4, HRV39 VP0, HRV39 live virus, and saline, respectively.

Figure 16A:
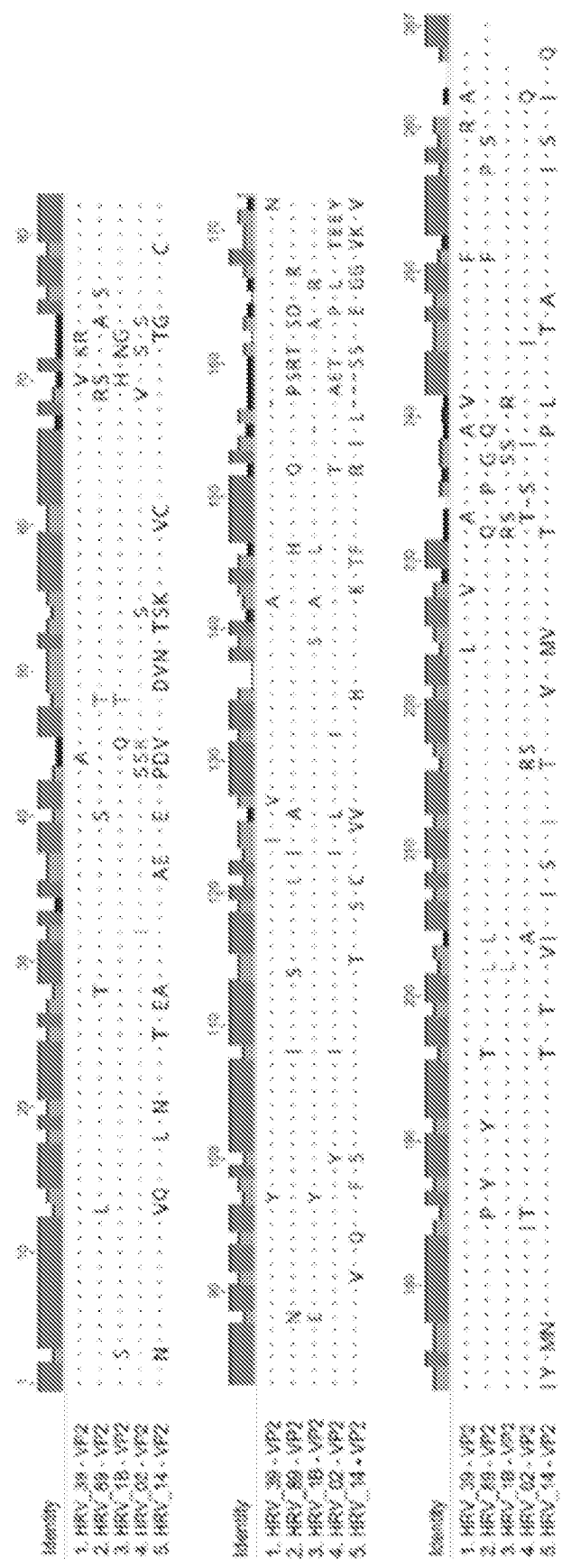

FIG. 16A: Alignments of the VP2 protein amino acid sequence of HRV types used in Example 4. Global view of the extent to which each amino acid is conserved within the types included. The height of the bar on the 'identity' line is directly related the degree to which that amino acid is conserved.

FIG. 16B: A heat map of the HRV types used in Example 4, displaying the percent identity at the amino acid level using pairwise comparisons.

FIG. 16C: Text amino acid alignments for the HRV types used in Example 4; HRV_39-VP2 (SEQ ID NO: 1), HRV_89-VP2 (SEQ ID NO:15), HRV_1B-VP2 (SEQ ID NO: 16), HRV_02-VP2 (SEQ ID NO: 17), and HRV_14-VP2 (SEQ ID NO: 18).

DETAILED DESCRIPTION

HRV VP2 Protein Constructs

HRV VP2 protein constructs useful as antigen component of immunogenic compositions for the induction of a cross-reactive immune response in a subject against Human Rhinovirus (HRV) are provided. As used herein, the term "antigen" refers to a molecule containing one or more epitopes (e.g., linear, conformational or both) that will stimulate a host's immune system to make a humoral and/or cellular antigen-specific immunological response (i.e. an immune response which specifically recognizes a naturally occurring polypeptide). An "epitope" is that portion of an antigen that determines its immunological specificity. T- and B-cell epitopes can be identified empirically (e.g. using PEPSCAN or similar methods). In the context of the invention, inducing a "cross-reactive immune response" means that an immune response is induced both against the HRV type from which the HRV antigen in the immunogenic composition, e.g. HRV VP2 protein of the invention, is derived (i.e. homologous immune response), and, against one or more HRV type(s) different from the HRV type from which the HRV antigen in the immunogenic composition is derived (i.e. heterologous immune response). In an embodiment, the immunogenic composition of the invention induces an immune response to both homologous and heterologous serotypes of human rhinoviruses.

For the purpose of the present invention, the terms "HRV VP2 protein construct", "human rhinovirus VP2 protein" or "HRV VP2 protein," or "VP2 protein" are used interchangeably and refer to any amino acid sequence corresponding to the amino acid sequence of the VP2 capsid protein of any HRV serotype. Immunogenic variants of an HRV VP2 protein construct are amino acid sequences with at least or exactly 75%, 77%, 80%, 85%, 90%, 95%, 97%, or 99% identity, over the entire length, to the native HRV VP2 sequence. The VP2 protein is about 270 amino acids long. Table 1 lists the uniprot accession numbers of complete genome polyprotein sequences for HRV serotypes selected from all three clades. Generally, the VP2 protein is situated between amino acids 70 and 339 of the polyprotein precursor. Thus, based on these sequences, the skilled person can derive wild type HRV VP2 and/or VP4 protein sequences for the HRV serotypes, for use in the present Examples and in the present invention.

Also known to the skilled person, the length of the amino acid sequence of the VP2 protein may vary slightly according to the HRV serotype. For example, HRV39 VP2 wild type protein corresponds to amino acid 70 to 334 of HRV39 VP0 wild type sequence (SEQ ID NO: 4).

Three HRV species have been identified in which the more than hundred types are classified, i.e. HRV-A, HRV-B and HRV-C.

The HRV-A species includes in particular the following serotypes: HRV1a, HRV1b, HRV2, HRV7, HRV8, HRV9, HRV10, HRV11, HRV12, HRV13, HRV15, HRV16, HRV18, HRV19, HRV20, HRV21, HRV22, HRV23, HRV24, HRV25, HRV28, HRV29, HRV30, HRV31, HRV32, HRV33, HRV34, HRV36, HRV38, HRV39, HRV40, HRV41, HRV43, HRV44, HRV45, HRV46, HRV47, HRV49, HRV50, HRV51, HRV53, HRV54, HRV55, HRV56, HRV57, HRV58, HRV59, HRV60, HRV61, HRV62, HRV63, HRV64, HRV65, HRV66, HRV67, HRV68, HRV71, HRV73, HRV74, HRV75, HRV76, HRV77, HRV78, HRV80, HRV81, HRV82, HRV85, HRV88, HRV89, HRV90, HRV94, HRV95, HRV96, HRV98, HRV100, HRV101, HRV102 and HRV103.

The HRV-B species includes in particular the following serotypes: HRV3, HRV4, HRV5, HRV6, HRV14, HRV17, HRV26, HRV27, HRV35, HRV37, HRV42, HRV48, HRV52, HRV69, HRV70, HRV72, HRV79, HRV83, HRV84, HRV86, HRV91, HRV92, HRV93, HRV97 and HRV99.

The HRV-C species includes in particular the following serotypes: HRV-C1, HRV-C2, HRV-C3, HRV-C4, HRV-C5, HRV-C6, HRV-C7, HRV-C8, HRV-C9, HRV-C10, HRV-C11, HRV-C12, HRV-C13, HRV-C14, HRV-C15, HRV-C16, HRV-C17, HRV-C18, HRV-C19, HRV-C20, HRV-C21, HRV-C22, HRV-C23, HRV-C24, HRV-C25, HRV-C26, HRV-C27, HRV-C28, HRV-C29, HRV-C30, HRV-C31, HRV-C32, HRV-C33, HRV-C34, HRV-C35, HRV-C36, HRV-C37, HRV-C38, HRV-C39, HRV-C40, HRV-C41, HRV-C42, HRV-C43, HRV-C44, HRV-C45, HRV-C46, HRV-C47, HRV-C48 and HRV-C49.

TABLE 1

| Clade | HRV | Uniprot accession |
|---|---|---|
| A | HRV1 | B9V432 |
| A | HRV10 | A5GZE7 |
| A | HRV100 | B9V496 |
| A | HRV101 | D2IW01 |
| A | HRV11 | A7KC06 |
| A | HRV12 | A7KC07 |
| A | HRV13 | B9V437 |
| A | HRV15 | A5GZE2 |
| A | HRV16 | Q82122 |
| A | HRV18 | B9V439 |
| A | HRV19 | B9V440 |
| A | HRV1B | P12916 |
| A | HRV2 | P04936 |
| A | HRV20 | B9V441 |
| A | HRV21 | B9V442 |
| A | HRV22 | B9V443 |
| A | HRV23 | A5GZE6 |
| A | HRV24 | B9V4B1 |
| A | HRV25 | B9V444 |
| A | HRV28 | A5GZF7 |
| A | HRV29 | B9V446 |
| A | HRV30 | B9V4A0 |
| A | HRV31 | B9V447 |
| A | HRV32 | B9V448 |
| A | HRV33 | B9V449 |
| A | HRV34 | B9V4B0 |
| A | HRV36 | A5GZF4 |
| A | HRV38 | A5GZE4 |
| A | HRV39 | Q5XLP5 |
| A | HRV40 | B9V450 |
| A | HRV41 | A5GZE0 |
| A | HRV43 | B9V452 |
| A | HRV44 | A5GZE8 |
| A | HRV45 | B9V453 |
| A | HRV46 | A5GZF5 |
| A | HRV47 | B9V454 |
| A | HRV49 | B9V455 |
| A | HRV50 | B9V456 |
| A | HRV51 | B9V457 |
| A | HRV53 | A5GZF6 |
| A | HRV54 | B9V459 |
| A | HRV55 | A5GZG0 |
| A | HRV56 | B9V461 |
| A | HRV57 | B9V462 |
| A | HRV58 | B9V463 |
| A | HRV59 | A5GZE9 |
| A | HRV60 | B9V464 |
| A | HRV61 | B9V465 |
| A | HRV62 | B9V466 |
| A | HRV63 | B9V467 |
| A | HRV64 | B9V4A2 |
| A | HRV65 | B9V468 |
| A | HRV66 | B9V469 |
| A | HRV67 | B9V470 |
| A | HRV68 | B9V471 |
| A | HRV7 | B9V497 |
| A | HRV71 | B9V473 |
| A | HRV73 | A5GZE1 |
| A | HRV74 | A5GZE3 |
| A | HRV75 | A5GZF9 |
| A | HRV76 | B9V4A3 |
| A | HRV77 | B9V475 |
| A | HRV78 | B9V4A4 |
| A | HRV8 | B9V434 |
| A | HRV80 | B9V477 |
| A | HRV81 | B9V478 |
| A | HRV82 | B9V481 |
| A | HRV85 | B9V484 |

TABLE 1-continued

| Clade | HRV | Uniprot accession |
|---|---|---|
| A | HRV88 | A5GZF3 |
| A | HRV89 | P07210 |
| A | HRV9 | B9V436 |
| A | HRV90 | B9V488 |
| A | HRV94 | B9V4A6 |
| A | HRV95 | B9V491 |
| A | HRV96 | B9V492 |
| A | HRV98 | B9V494 |
| B | HRV14 | P03303 |
| B | HRV17 | A7KC12 |
| B | HRV26 | B9V445 |
| B | HRV27 | A7KC13 |
| B | HRV3 | A7KC14 |
| B | HRV35 | B9V4A8 |
| B | HRV37 | A7KC15 |
| B | HRV4 | A5GZD9 |
| B | HRV42 | B9V451 |
| B | HRV48 | A5GZD7 |
| B | HRV5 | B9V433 |
| B | HRV52 | B9V458 |
| B | HRV6 | A5GZD5 |
| B | HRV69 | B9V472 |
| B | HRV70 | A5GZD8 |
| B | HRV72 | D6PT65 |
| B | HRV79 | B9V476 |
| B | HRV83 | B9V482 |
| B | HRV84 | B9V483 |
| B | HRV86 | B9V485 |
| B | HRV91 | B9V489 |
| B | HRV92 | B9V490 |
| B | HRV93 | A7KC17 |
| B | HRV97 | B9V493 |
| B | HRV99 | B9V495 |
| C | HRVC-11 | C5HDF8 |
| C | HRVC-STRAIN CU072 | E9LS20 |
| C | HRVC-CU184 | E9LS23 |
| C | HRVC-15 | E5D8F2 |
| C | HRVC-24 | A8S322 |
| C | HRVC-25 | A8S330 |
| C | HRVC-26 | A8S334 |
| C | HRVC-STRAIN NAT045 | A7TUB2 |
| C | HRVC-STRAIN NAT001 | A7TUB1 |
| C | HRVC-STRAIN NY-074 | A0MHB7 |
| C | HRVC-04 | C7DUC6 |
| C | HRVC-10 | C7DUC7 |
| C | HRVC-03 | A4UHT9 |
| C | HRVC-STRAIN QCE | C9DDK2 |
| C | HRVC-54 | A0A0B5HPB2 |
| C | HRVC-35 | H8Y6P9 |

HRV types may also be grouped according to receptor usage, into minor-group viruses and major-group viruses. Minor-group viruses, such as HRV2, use the low-density lipoprotein receptor family as receptor. They are acid labile and have an absolute dependence on low pH for uncoating. Major-group viruses, such as HRV14 and HRV16, use intercellular adhesion molecule 1 (ICAM-1) as receptor. They are generally acid labile but, unlike the minor-group viruses, do not have an absolute dependence on low pH for un-coating. As well-known to the skilled person, minor-group HRVs include 11 serotypes, including HRV1A, HRV1B, HRV2, HRV23, HRV25, HRV29, HRV30, HRV31, HRV44, HRV47, HRV49 and HRV62.

For the purpose of the invention, the VP2 protein of any of the HRV types listed herein can be used. In one embodiment, the HRV VP2 protein is the HRV VP2 protein of HRV39, HRV1b, HRV2, HRV3, HRV14, HRV25 or HRV28, or, an immunogenic variant thereof. In a specific embodiment, the HRV VP2 protein is VP2 protein of HRV39 (SEQ ID NO: 1) or an immunogenic variant thereof with at least 90%, 95%, 97%, or 99% identity, over the entire length, to SEQ ID NO:1.

Identity or homology with respect to a sequence is defined herein as the percentage of amino acid residues in the candidate sequence that are identical with the reference amino acid sequence after aligning the sequences and introducing gaps, if necessary, to achieve the maximum percent sequence identity, and not considering any conservative substitutions as part of the sequence identity.

Sequence identity can be determined by standard methods that are commonly used to compare the similarity in position of the amino acids of two polypeptides. Using a computer program such as BLAST or FASTA, two polypeptides are aligned for optimal matching of their respective amino acids (either along the full length of one or both sequences or along a pre-determined portion of one or both sequences). The programs provide a default opening penalty and a default gap penalty, and a scoring matrix such as PAM 250 [a standard scoring matrix; see Dayhoff et al., in Atlas of Protein Sequence and Structure, vol. 5, supp. 3 (1978)] can be used in conjunction with the computer program. For example, the percent identity can then be calculated as: the total number of identical matches multiplied by 100 and then divided by the sum of the length of the longer sequence within the matched span and the number of gaps introduced into the shorter sequences in order to align the two sequences.

Where a sequence is referred to herein by a UniProt or Genbank accession code, the sequence referred to is the version as of the filing date of the present application.

In one embodiment, HRV VP2 proteins described herein are suitably isolated. An "isolated" HRV VP2 protein is one that is removed from its original environment. Similarly, polynucleotides described herein are suitably isolated. For example, a naturally occurring protein is isolated if it is separated from some or all of the coexisting materials in the natural system. A polynucleotide is considered isolated if, for example, it is cloned into a vector that is not a part of its natural environment or if it is comprised within cDNA.

In one embodiment, an immunogenic variant of a HRV VP2 protein corresponds to an HRV VP2 protein wherein an amino acid sequence of up to 25, or, up to 20 amino acids may be inserted, substituted or deleted, e.g. 1, 2, 3, 4, 5, 6, 7, 8, 9, 10, 12, 13, 14, 15, 16, 17, 18, 19 or 20 amino acid(s). In a more specific embodiment, such insertion, substitution or deletion is located in those parts of the amino acid sequences of the VP2 protein that correspond to highly variable regions of the HRV VP2 protein. Regions in the HRV VP2 protein suitable for such insertion, substitution or deletion includes aa155-170 (i.e. NIm-II loop), aa134-146, aa232-238 and aa72-75, each of which the numbering is based on HRV39 VP2 full length sequence (SEQ ID NO: 1). In a particular embodiment, an insertion, deletion and/or substitution is located at aa155-170 (i.e. NIm-II loop). In a specific embodiment, the HRV VP2 protein is VP2 protein of HRV39 having a mutation in its NIm-II loop (SEQ ID NO: 2) or an immunogenic variant thereof with at least 90%, 95%, 97%, or 99% identity to SEQ ID NO:2, over the entire length. Alternatively, an insertion, deletion and/or substitution is located at the VP2 carboxy terminal.

In a further embodiment, a HRV peptide is inserted or substituted in one of said highly variable regions of the HRV VP2 protein; the peptide is derived from one of the HRV capsid proteins VP1, VP2, VP3 or VP4, and is capable of inducing a cross-reactive and/or cross-neutralising immune response against two or more HRV serotypes. Such peptides are selected or derived from conserved regions of the structural proteins of human rhinoviruses. A cross-reactive and/or neutralizing response can be achieved when the HRV amino acid sequence is of limited length. Thus the HRV peptide may consist of a fragment of 5 to 40 contiguous amino acids, or 8 to 30 contiguous amino acids, from a wild-type full-length HRV capsid protein (VP1, VP2, VP3 or VP4). Favorably, the HRV peptide consists consist of no more than 20 amino acids, such as 8 to 20 amino acids, e.g. 16 amino acids. In any embodiment, a HRV peptide or variant thereof will have a minimum length of 8 amino acids.

The VP2 protein of the invention may include or comprise HRV amino acid fragments or peptides that have been described in the literature. For example, it has been demonstrated that antibodies induced with recombinant HRV-14 or -89 VP1 amino acid fragments spanning amino acids 147-162 of HRV14 VP1 exhibit specific and cross-neutralizing activity (McCray & Werner, 1998 Nature Oct 22-28; 329(6141):736-8; Edlmayr et al., 2011, Eur. Respir. J. 37:44-52). It has been observed that the rhinovirus capsid structure is dynamic and appears to oscillate between two different structural states: one in which the VP4 is deeply buried, and the other where the N-terminus of VP4 and VP1 are accessible to proteases (Lewis et al 1998 Proc Natl Acad Sci USA. 95(12):6774-8). Antibodies raised against the 30 N terminal amino acids of VP4 but not VP1 were found to successfully neutralise viral infectivity in vitro (Katpally et al 2009, J Virol. 83(14):7040-8.). Antibodies raised against the N terminal 30 amino acids of VP4 were found to neutralise HRV14, HRV16 and HRV29. In addition, antibodies raised to a consensus sequence of the first 24 residues from rhinovirus VP4 also had some cross-neutralising activity (Katpally et al, 2009, J Virol. 83(14):7040-8.).

Other descriptions of HRV peptides and/or epitopes in the literature can be found in: Niespodziana et al 2012 (The FASEB Journal. Vol 26, 1001-1008) in which a response against an N terminal 20 mer from VP1 was not a neutralising response, i.e. non-protective epitope; Miao et al 2009 (J. Clin. Micorbiol. Vol 47, No 10, 3108-3113)—MAbs generated against the N terminal part of enterovirus VP1 which is highly conserved are useful in recognizing a broad range of enteroviruses; WO 2006/078648 relating to peptides vaccines against HRV derived from the transiently exposed regions of VP4 in particular amino acids 1-31 or 1-24 of VP4; WO 2011/050384 relating to peptides from the N terminus of VP1 including amino acids 1-8; WO 2008/057158 relating to NIm IV of rhinovirus, in particular a peptide comprising amino acids 277-283 or 275-285 from the carboxyl terminal region of VP1, in particular from HRV-14.

Further HRV peptides have been identified derived from the N-terminal sequences of VP1 and VP4, i.e. HRV amino acid fragments comprising amino acids 32-45 of VP1 and HRV amino acid fragments comprising amino acids 1-16 of VP4, or variants thereof having 1-4 amino acid additions or deletions at either end and/or 1-2 amino acid substitutions or additions or deletions with the peptide sequence. Where a variant of a peptide sequence has 1-4 amino acid additions or deletions at either end and/or 1-2 amino acid substitutions or additions or deletions within the peptide sequence, this means that the variant has at least one amino acid difference compared to the reference peptide sequence, which may include between 0 and 4 amino acid additions or deletions at one end and between 0 and 4 additions or deletions at the other end and between 0 and 2 amino acid substitutions or additions or deletions within the sequence.

In one embodiment a peptide consists of at least 8 and no more than 20 amino acids from the N terminus of VP4, which HRV peptide includes amino acids 1-16 of VP4 or a variant of amino acids 1-16 having 1-4 amino acid additions or deletions at either end and/or 1-2 amino acid substitutions or additions or deletions within the peptide sequence. In a particular embodiment the VP4 HRV peptide consists of amino acids 1-16 of VP4 or a variant having one, two, three, or four amino acid additions or deletions or substitutions. Further specific VP4 HRV amino acid fragments include, for example, amino acids 1 to [16-20], amino acids 2 to [17-21], 3 to [18-22], 4 to [19-23], 5 to [20-24] wherein it will be understood that the numbers in square brackets include all numbers in the specified range individually. Favorably, the VP4 HRV peptide consists of no more than 16 contiguous amino acids from VP4. It should be understood that the numbering of the VP4 HRV peptide or any (recombinantly expressed) peptide or protein as used herein is independent of methionine due to the start codon.

In another embodiment an HRV peptide consists of at least 8 and no more than 40 amino acids from the N terminal region of VP1, which HRV peptide includes amino acids 32-45 of VP1 or a variant of amino acids 32-45 having 1-4 amino acid additions or deletions at either end and/or 1-2 amino acid substitutions or additions or deletions within the peptide sequence. In a particular embodiment the VP1 HRV amino acid fragment consists of amino acids 32-45 of VP4 or a variant having one, two, three, or four amino acid additions or deletions or substitutions. VP1 peptides include for example amino acids [5-35] to 45, [6-35] to 46, [7-35] to 47, [8-35] to 48, [9-35] to 49 and similarly 32 to [45-72], 33 to [45-73], 34 to [45-74], 35 to [45-75] and 36 to [45-76] wherein the numbers in square brackets include all numbers in the specified range individually.

HRV peptides for the purpose of the invention thus include:

amino acids 147-162 of HRV14 VP1 or a variant of amino acids 147-162 of HRV14 VP1 having 1-4 amino acid additions or deletions at either end and/or 1-2 amino acid substitutions or additions or deletions within the peptide sequence;

amino acids 1-30 of HRV14 VP4 or a variant of amino acids 1-30 of HRV14 VP4 having 1-4 amino acid additions or deletions at either end and/or 1-2 amino acid substitutions or additions or deletions within the peptide sequence;

amino acids 1-24 of HRV14 VP4 or a variant of amino acids 1-24 of HRV14 VP4 having 1-4 amino acid additions or deletions at either end and/or 1-2 amino acid substitutions or additions or deletions within the peptide sequence;

amino acids 1-8 of HRV14 VP1 or a variant of amino acids 1-8 of HRV14 VP1 having 1-4 amino acid additions or deletions at either end and/or 1-2 amino acid substitutions or additions or deletions within the peptide sequence;

amino acids 277-283 of HRV14 VP1 or a variant of amino acids 277-283 of HRV14 VP1 having 1-4 amino acid additions or deletions at either end and/or 1-2 amino acid substitutions or additions or deletions within the peptide sequence;

amino acids 275-285 of HRV14 VP1 or a variant of amino acids 275-285 of HRV14 VP1 having 1-4 amino acid additions or deletions at either end and/or 1-2 amino acid substitutions or additions or deletions within the peptide sequence;

amino acids 32-45 of VP1 or a variant of amino acids 32-45 having 1-4 amino acid additions or deletions at either end and/or 1-2 amino acid substitutions or additions or deletions within the peptide sequence;

amino acids 1-16 of VP4 or a variant of amino acids 1-16 having 1-4 amino acid additions or deletions at either end and/or 1-2 amino acid substitutions or additions or deletions within the peptide sequence.

In a particular embodiment, the HRV peptide is derived from VP1 and has or comprises an amino acid sequence selected from:

```
HRV14 (B):
                                       (SEQ ID NO: 5)
32-PILTANETGATMPV-45

HRV8 (A-M):
                                       (SEQ ID NO: 6)
32-PALDAAETGHTSSV-45

HRV25 (A-m):
                                       (SEQ ID NO: 7)
32-PILDAAETGHTSNV-45

HRV_C_026:
                                       (SEQ ID NO: 8)
32-QALGAVEIGATADV-45
``` or a variant thereof having 1-4 amino acid additions or deletions at either end and/or 1-2 amino acid substitutions or additions or deletions within the amino acid sequence.

In another particular embodiment, the HRV peptide is derived from VP4 and has or comprises an amino acid sequence selected from:

```
HRV14 (B):
                                       (SEQ ID NO: 9)
1-GAQVSTQKSGSHENQN-16

HRV100 (A-M):
                                       (SEQ ID NO: 10)
1-GAQVSRQNVGTHSTQN-16

HRV_C_026:
                                       (SEQ ID NO: 11)
1-GAQVSRQSVGSHETMI-16
``` or a variant thereof having 1-4 amino acid additions or deletions at either end and/or 1-2 amino acid substitutions or additions or deletions within the amino acid sequence. For the purpose of the present invention, the immunogenic variants consist of or comprises an amino acid sequence with at least or exactly 75%, 77%, 80%, 85%, 90%, 95%, 97%, or 99% identity, over the entire length, to the native sequence.

In a further particular embodiment, HRV2 VP2 derived peptides may be introduced in the VP2 protein, wherein the HRV2 VP2 derived peptide is selected from:

```
                                      (SEQ ID NO: 12)
SSKGWWWKLPDALKDMGIFGENMFYHYLGRS (HRV2 VP2 aa 143-
173), (SEQ ID NO: 13)
IPEHQIASALHGNVNVGYNYTHPGETGREVK (HRV2 VP2 aa 196-
226),
and (SEQ ID NO: 14)
INTIPITISISPMCAEFSGARAKRQGLPVFI (HRV2 VP2 aa 306-
336).
```

In one embodiment, the composition does not comprise a VP4 protein (or polynucleotide comprising a nucleic acid sequence encoding a HRV VP4 protein). For the purpose of the present invention, the term "human rhinovirus VP4 protein" or "HRV VP4 protein" or "VP4 protein" refers to any amino acid sequence corresponding to the amino acid sequence of the VP4 capsid protein of any HRV serotype as well as a variant thereof, wherein the variant is at least 90% identical to the VP4 amino acid sequence of a HRV.

The HRV VP2 protein may be chemically synthesized using standard techniques or produced recombinantly.

Adjuvanted HRV VP2 Protein

In one embodiment, the immunogenic composition or vaccine comprises the HRV VP2 protein as defined herein and in combination with an adjuvant, such as a Th1 adjuvant.

For the purpose of the present invention, the term "adjuvant" refers to a compound or composition that enhances the immune response to an antigen, such as the immune response to an HRV VP2 protein in a human subject. Examples of such adjuvants include but are not limited to inorganic adjuvants (e.g. inorganic metal salts such as aluminium phosphate or aluminium hydroxide), organic adjuvants (e.g. saponins, such as QS21, or squalene), oil-based adjuvants (e.g. Freund's complete adjuvant and Freund's incomplete adjuvant), cytokines (e.g. IL-1β, IL-2, IL-7, IL-12, IL-18, GM-CFS, and INF-γ), particulate adjuvants (e.g. immuno-stimulatory complexes (ISCOMS), liposomes, or biodegradable microspheres), virosomes, bacterial adjuvants (e.g. monophosphoryl lipid A, such as 3-de-O-acylated monophosphoryl lipid A (3D-MPL), or muramyl peptides), synthetic adjuvants (e.g. non-ionic block copolymers, muramyl peptide analogues, or synthetic lipid A), synthetic polynucleotides adjuvants (e.g. polyarginine or polylysine), and immunostimulatory oligonucleotides containing unmethylated CpG dinucleotides ("CpG").

In one embodiment, the adjuvant is a saponin-containing adjuvant. A suitable saponin for use in the present invention is Quil A and its derivatives. Quil A is a saponin preparation isolated from the South American tree *Quillaja saponaria* Molina and was first described as having adjuvant activity by Dalsgaard et al. in 1974 ("Saponin adjuvants", Archiv. für die gesamte Virusforschung, Vol. 44, Springer Verlag, Berlin, p 243-254). Purified fragments of Quil A have been isolated by HPLC which retain adjuvant activity without the toxicity associated with Quil A (EP 0 362 278), for example QS7 and QS21 (also known as QA7 and QA21). QS-21 is a natural saponin derived from the bark of *Quillaja saponaria* Molina, which induces CD8+ cytotoxic T cells (CTLs), Th1 cells and a predominant IgG2a antibody response and is a preferred saponin in the context of the present invention. In a suitable form of the present invention, the saponin adjuvant within the immunogenic composition is a derivative of *Quillaja saponaria* Molina quil A, preferably an immunologically active fraction of Quil A, such as QS-7, QS-17, QS-18 or QS-21, suitably QS-21.

In one embodiment, the saponin comprises a combination of saponin fractions such as disclosed in WO 1996/011711. Alternatively (semi-)synthetic saponins are considered useful such as the ones reviewed by Govind Ragupathi et al. (Expert Rev Vaccines 2011; 10(4):463-470).

The saponin is typically provided in its less reactogenic composition where it is quenched with an exogenous sterol, such as cholesterol. Suitable sterols include β-sitosterol, stigmasterol, ergosterol, ergocalciferol and cholesterol. These sterols are well known in the art, for example cholesterol is disclosed in the Merck Index, 11th Edn., page 341, as a naturally occurring sterol found in animal fat. Several particular forms of less reactogenic compositions wherein QS21 is quenched with exogenous sterol such as cholesterol exist. In one embodiment, the saponin/sterol is presented in a liposomal formulation structure. Methods for obtaining saponin/sterol in a liposomal formulation are described in WO 96/33739, in particular Example 1.

A saponin, such as QS21, can be used at amounts between 1 and 100 μg per human dose of the adjuvant composition. QS21 may be used at a level of about 50 μg, such as at least 40 μg, at least 45 μg or at least 49 μg, or, less than 100 μg, less than 80 μg, less than 60 μg, less than 55 μg or less than 51 μg. Examples of suitable ranges are between 40-60 μg, suitably between 45-55 μg or between 49 and 51 μg or 50 μg. In a further embodiment, the human dose of the adjuvant composition comprises QS21 at a level of about 25 μg, such as at least 20 μg, at least 21 μg, at least 22 μg or at least 24 μg, or, less than 30 μg, less than 29 μg, less than 28 μg, less than 27 μg or less than 26 μg. Examples of lower ranges include between 20-30 μg, suitably between 21-29 μg or between 22-28 μg or between 28 and 27 μg or between 24 and 26 μg, or 25 μg.

Where the active saponin fraction is QS21 and a sterol is included, the ratio of QS21:sterol will typically be in the order of 1:100 to 1:1 (w/w), suitably between 1:10 to 1:1 (w/w), and preferably 1:5 to 1:1 (w/w). Suitably excess sterol is present, the ratio of QS21:sterol being at least 1:2 (w/w). In one embodiment, the ratio of QS21:sterol is 1:5 (w/w). In a specific embodiment, the sterol is cholesterol.

In one embodiment, the adjuvant comprises a TLR-4 agonist (also referred to as TLR-4 ligand). A suitable example of a TLR-4 agonist is a lipopolysaccharide, suitably a non-toxic derivative of lipid A, particularly monophosphoryl lipid A or more particularly 3-Deacylated monophosphoryl lipid A (3D-MPL).

3D-MPL is sold under the name MPL by GlaxoSmithKline Biologicals N.A. and is referred throughout the document as MPL or 3D-MPL. See, for example, U.S. Pat. Nos. 4,436,727; 4,877,611; 4,866,034 and 4,912,094. 3D-MPL primarily promotes CD4+ T cell responses with an IFNg (Th1) phenotype. 3D-MPL can be produced according to the methods described in GB 2 220 211 A. Chemically it is a mixture of 3-deacylated monophosphoryl lipid A with 4, 5 or 6 acylated chains. In the compositions of the present invention small particle 3D-MPL may be used to prepare the adjuvant. Small particle 3D-MPL has a particle size such that it may be sterile-filtered through a 0.22 μm filter. Such preparations are described in WO 94/21292.

Other TLR-4 ligands which can be used are aminoalkyl glucosaminide phosphates (AGPs) such as those described in WO98/50399 or U.S. Pat. No. 6,303,347 (processes for preparation of AGPs are also described), suitably RC527 or RC529 or pharmaceutically acceptable salts of AGPs as described in U.S. Pat. No. 6,764,840. Further suitable AGPs are described in WO 2004/062599. Some AGPs are TLR-4 agonists, and some are TLR-4 antagonists. Both are thought to be useful as adjuvants.

Other suitable TLR-4 ligands are as described in WO2003/011223 and in WO 2003/099195, such as compound I, compound II and compound III described on pages 4-5 of WO2003/011223 or on pages 3-4 of WO2003/099195 and in particular those compounds described in WO2003/011223 as ER803022, ER803058, ER803732, ER804053, ER804057m ER804058, ER804059, ER804442, ER804680 and ER804764. For example, one suitable TLR-4 ligand is ER804057.

Other TLR-4 ligands which may be of use in the present invention include Glucopyranosyl Lipid Adjuvant (GLA) such as described in WO2008/153541 or WO2009/143457 or the literature articles Coler R N et al. (Development and Characterization of Synthetic Glucopyranosyl Lipid Adjuvant System as a Vaccine Adjuvant, PLoS ONE 6(1): e16333. doi:10.1371/journal.pone.0016333, 2011) and Arias M A et al. (Glucopyranosyl Lipid Adjuvant (GLA), a Synthetic TLR4 Agonist, Promotes Potent Systemic and Mucosal Responses to Intranasal Immunization with HIVgp140, PLoS ONE 7(7): e41144. doi:10.1371/journal.pone.0041144, 2012). WO2008/153541 or WO2009/143457 are incorporated herein by reference for the purpose of defining TLR-4 ligands which may be of use in the present invention.

A TLR-4 ligand such as a lipopolysaccharide, such as 3D-MPL, can be used at amounts between 1 and 100 μg per human dose of the adjuvant composition. 3D-MPL may be used at a level of about 50 μg, such as at least 40 μg, at least 45 μg or at least 49 μg, or, less than 100 μg, less than 80 μg, less than 60 μg, less than 55 μg or less than 51 μg. Examples of suitable ranges are between 40-60 μg, suitably between 45-55 μg or between 49 and 51 μg or 50 μg. In a further embodiment, the human dose of the adjuvant composition comprises 3D-MPL at a level of about 25 μg, such as at least 20 μg, at least 21 μg, at least 22 μg or at least 24 μg, or, less than 30 μg, less than 29 μg, less than 28 μg, less than 27 μg or less than 26 μg. Examples of lower ranges include between 20-30 μg, suitably between 21-29 μg or between 22-28 μg or between 28 and 27 μg or between 24 and 26 μg, or 25 μg.

In one embodiment, the adjuvant comprises a TLR4 agonist, such as 3D-MPL, formulated with an aluminum salt, such as aluminum hydroxide or aluminum phosphate.

In a specific embodiment, the adjuvant comprises both a saponin and a TLR4 agonist. In a specific example, the adjuvant comprises QS21 and 3D-MPL. In an alternative embodiment the adjuvant comprises QS21 and GLA.

When both a TLR4 agonist and a saponin are present in the adjuvant, then the weight ratio of TLR4 agonist to saponin is suitably between 1:5 to 5:1, suitably 1:1. For example, where 3D-MPL is present at an amount of 50 μg or 25 μg, then suitably QS21 may also be present at an amount of 50 μg or 25 μg per human dose of the adjuvant.

In an embodiment, the saponin, optionally with TLR4 agonist, is delivered in a liposomal formulation. By "liposomal formulation" is meant the saponin (and optionally TLR-4 agonist) is formulated with liposomes, or, stated alternatively, presented in a liposome based composition. The liposomes intended for the present invention contain a neutral lipid or consist essentially of neutral lipid. By "neutral lipid" is understood that the overall net charge of the lipid is (approximately) zero. The lipid may therefore be non-ionic overall or may be zwitterionic. In one embodiment the liposomes comprises a zwitterionic lipid. Examples of suitable lipids are phospholipids such as phosphatidylcholine species. In one embodiment the liposomes contain phosphatidylcholine as a liposome forming lipid which is suitably non-crystalline at room temperature. Examples of such non-crystalline phosphatidylcholine lipids include egg yolk phosphatidylcholine, dioleoyl phosphatidylcholine (DOPC) or dilauryl phosphatidylcholine (DLPC). In a particular embodiment, the liposomes of the present invention contain DOPC, or, consist essentially of DOPC. The liposomes may also contain a limited amount of a charged lipid which increases the stability of the liposome-saponin structure for liposomes composed of saturated lipids. In these cases the amount of charged lipid is suitably 1-20% w/w, preferably 5-10% w/w of the liposome composition. Suitable examples of such charged lipids include phosphatidylglycerol and phosphatidylserine. Suitably, the neutral liposomes will contain less than 5% w/w charged lipid, such as less than 3% w/w or less than 1% w/w. In one particular embodiment, the liposomal formulation comprises cholesterol as sterol.

Nucleic Acid Constructs Encoding a Polypeptide Comprising a HRV VP2 Protein

In one embodiment, the immunogenic composition or vaccine comprises the polynucleotide comprising a nucleic acid sequence encoding the HRV VP2 protein as defined herein. In a further embodiment, the nucleic acid sequence encoding the HRV VP2 protein is placed under control of elements enabling its expression in a cell, such as in a mammalian cell.

In one embodiment, the nucleic acid sequence is incorporated into a viral vector, such as an adenoviral vector. Thus, in a specific embodiment, the composition comprises adenoviral vector comprising a transgene encoding the HRV VP2 protein as defined herein.

Adenovirus has been widely used for gene transfer applications due to its ability to achieve highly efficient gene transfer in a variety of target tissues and large transgene capacity. Adenoviral vectors of use in the present invention may be derived from a range of mammalian hosts. Over 100 distinct serotypes of adenovirus have been isolated which infect various mammalian species. These adenoviral serotypes have been categorized into six subgenera (A-F; B is subdivided into B1 and B2) according to sequence homology and ability to agglutinate red blood cells (Tatsis and Ertl, Molecular Therapy (2004) 10:616-629).

In one embodiment, the adenoviral vector of the present invention is derived from a human adenovirus. Examples of such human-derived adenoviruses are Ad1, Ad2, Ad4, Ad5, Ad6, Ad11, Ad 24, Ad34, Ad35, particularly Ad5, Ad11 and Ad35. Although Ad5-based vectors have been used extensively in a number of gene therapy trials, there may be limitations on the use of Ad5 and other human group C adenoviral vectors due to preexisting immunity in the general population due to natural infection. Ad5 and other human group C members tend to be among the most seroprevalent serotypes. Additionally, immunity to existing vectors may develop as a result of exposure to the vector during treatment. These types of preexisting or developed immunity to seroprevalent vectors may limit the effectiveness of gene therapy or vaccination efforts.

Therefore, in another embodiment, the adenoviral vector is derived from a nonhuman simian adenovirus, also referred to simply as a simian adenovirus. Numerous adenoviruses have been isolated from nonhuman simians such as chimpanzees, bonobos, rhesus macaques and gorillas, and vectors derived from these adenoviruses induce strong immune responses to transgenes encoded by these vectors (Colloca et al. (2012) Sci. Transl. Med. 4:1-9; Roy et al. (2004) Virol.324: 361-372; Roy et al. (2010) J. of Gene Med. 13:17-25). Certain advantages of vectors based on nonhuman simian adenoviruses include the relative lack of cross-neutralising antibodies to these adenoviruses in the target human population. For example, cross-reaction of certain chimpanzee adenoviruses with pre-existing neutralizing antibody responses is only present in 2% of the target human population compared with 35% in the case of certain candidate human adenovirus vectors.

In specific embodiments, the adenoviral vector is derived from a non-human adenovirus, such as a simian adenovirus and in particular a chimpanzee adenovirus such as ChAd3, ChAd63, ChAd83, ChAd155, Pan 5, Pan 6, Pan 7 (also referred to as C7) or Pan 9. Examples of such strains are described in WO03/000283, WO2010/086189 and GB1510357.5 and are also available from the American Type Culture Collection, 10801 University Boulevard, Manassas, Va. 20110-2209, and other sources. Alternatively, adenoviral vectors may be derived from nonhuman simian adenoviruses isolated from bonobos, such as PanAd1, PanAd2 or PanAd3. Examples of such vectors described herein can be found for example in WO2005/071093 and WO2010/086189. Adenoviral vectors may also be derived from adenoviruses isolated from gorillas as described in WO2013/52799, WO2013/52811 and WO2013/52832.

Adenoviral vectors may be used to deliver desired nucleic acid or protein sequences, for example heterologous (gene) sequences, for in vivo expression. A vector may include any genetic element including naked DNA, a phage, transposon, cosmid, episome, plasmid, or a virus for the delivery. By "expression cassette" is meant the combination of a selected heterologous gene (transgene) and the other regulatory elements necessary to drive translation, transcription and/or expression of the gene product in a host cell.

Typically, an adenoviral vector is designed such that the expression cassette is located in a nucleic acid molecule which contains other adenoviral sequences in the region native to a selected adenoviral gene. The expression cassette may be inserted into an existing gene region to disrupt the function of that region, if desired. Alternatively, the expression cassette may be inserted into the site of a partially or fully deleted adenoviral gene. For example, the expression cassette may be located in the site of a mutation, insertion or deletion which renders non-functional at least one gene of a genomic region selected from the group consisting of E1A, E1B, E2A, E2B, E3 and E4. The term "renders non-functional" means that a sufficient amount of the gene region is removed or otherwise disrupted, so that the gene region is no longer capable of producing functional products of gene expression. If desired, the entire gene region may be removed (and suitably replaced with the expression cassette). Suitably, E1 genes of adenovirus are deleted and replaced with an expression cassette consisting of the promoter of choice, cDNA sequence of the gene of interest and a poly A signal, resulting in a replication defective recombinant virus.

In another embodiment, the nucleic acid sequence is incorporated into a self-amplifying mRNA vector (hereinafter referred to as SAM). SAM RNA molecules are well known in the art and can be produced by using replication elements derived from, e.g., alphaviruses, and substituting the structural viral proteins with a nucleotide sequence encoding a protein of interest. A SAM RNA molecule is typically a +-strand molecule which can be directly translated after delivery to a cell, and this translation provides a RNA-dependent RNA polymerase which then produces both antisense and sense transcripts from the delivered RNA. Thus the delivered RNA leads to the production of multiple daughter RNAs. These daughter RNAs, as well as collinear subgenomic transcripts, may be translated themselves to provide in situ expression of an encoded antigen (i.e. a HRV VP2 protein construct), or may be transcribed to provide further transcripts with the same sense as the delivered RNA which are translated to provide in situ expression of the antigen. The overall result of this sequence of transcriptions is a huge amplification in the number of the introduced replicon RNAs and so the encoded antigen becomes a major polypeptide product of the cells.

One suitable system for achieving self-replication in this manner is to use an alphavirus-based replicon. These replicons are +-stranded RNAs which lead to translation of a replicase (or replicase-transcriptase) after delivery to a cell. The replicase is translated as a polyprotein which auto- cleaves to provide a replication complex which creates genomic-strand copies of the +-strand delivered RNA. These −-strand transcripts can themselves be transcribed to give further copies of the +-stranded parent RNA and also to give a subgenomic transcript which encodes the antigen. Translation of the subgenomic transcript thus leads to in situ expression of the antigen by the infected cell. Suitable alphavirus replicons can use a replicase from a Sindbis virus, a Semliki forest virus, an eastern equine encephalitis virus, a Venezuelan equine encephalitis virus, etc. Mutant or wild-type virus sequences can be used e.g. the attenuated TC83 mutant of VEEV has been used in replicons, see the following reference: WO2005/113782.

In certain embodiments, the SAM RNA molecule described herein encodes (i) a RNA-dependent RNA polymerase which can transcribe RNA from the SAM RNA molecule and (ii) a HRV VP2 protein antigen as described herein. The polymerase can be an alphavirus replicase e.g. comprising one or more of alphavirus proteins nsP1, nsP2, nsP3 and nsP4.

Whereas natural alphavirus genomes encode structural virion proteins in addition to the non-structural replicase polyprotein, in certain embodiments, the SAM RNA molecules do not encode alphavirus structural proteins. Thus, the SAM RNA can lead to the production of genomic RNA copies of itself in a cell, but not to the production of RNA-containing virions. The inability to produce these virions means that, unlike a wild-type alphavirus, the SAM RNA molecule cannot perpetuate itself in infectious form. The alphavirus structural proteins which are necessary for perpetuation in wild-type viruses are absent from SAM RNAs of the present disclosure and their place is taken by gene(s) encoding the immunogen of interest, such that the subgenomic transcript encodes the immunogen rather than the structural alphavirus virion proteins.

Thus a SAM RNA molecule useful with the invention may have two open reading frames. The first (5') open reading frame encodes a replicase; the second (3') open reading frame encodes an antigen. In some embodiments the RNA may have additional (e.g. downstream) open reading frames e.g. to encode further antigens or to encode accessory polypeptides.

In certain embodiments, the SAM RNA molecule disclosed herein has a 5' cap (e.g. a 7-methylguanosine). This cap can enhance in vivo translation of the RNA. In some embodiments the 5' sequence of the SAM RNA molecule must be selected to ensure compatibility with the encoded replicase.

A SAM RNA molecule may have a 3' poly-A tail. It may also include a poly-A polymerase recognition sequence (e.g. AAUAAA) near its 3' end.

SAM RNA molecules can have various lengths but they are typically 5000-25000 nucleotides long. SAM RNA molecules will typically be single-stranded. Single-stranded RNAs can generally initiate an adjuvant effect by binding to TLR7, TLR8, RNA helicases and/or PKR. RNA delivered in double-stranded form (dsRNA) can bind to TLR3, and this receptor can also be triggered by dsRNA which is formed either during replication of a single-stranded RNA or within the secondary structure of a single-stranded RNA.

The SAM RNA can conveniently be prepared by in vitro transcription (IVT). IVT can use a (cDNA) template created and propagated in plasmid form in bacteria, or created synthetically (for example by gene synthesis and/or polymerase chain-reaction (PCR) engineering methods). For instance, a DNA-dependent RNA polymerase (such as the bacteriophage T7, T3 or SP6 RNA polymerases) can be used to transcribe the SAM RNA from a DNA template. Appropriate capping and poly-A addition reactions can be used as required (although the replicon's poly-A is usually encoded within the DNA template). These RNA polymerases can have stringent requirements for the transcribed 5' nucleotide(s) and in some embodiments these requirements must be matched with the requirements of the encoded replicase, to ensure that the IVT-transcribed RNA can function efficiently as a substrate for its self-encoded replicase.

A SAM RNA can include (in addition to any 5' cap structure) one or more nucleotides having a modified nucleobase. A RNA used with the invention ideally includes only phosphodiester linkages between nucleosides, but in some embodiments it can contain phosphoramidate, phosphorothioate, and/or methylphosphonate linkages.

The SAM RNA molecule may encode a single heterologous polypeptide antigen (i.e. a HRV VP2 protein antigen as described herein) or, optionally, two or more heterologous antigens linked together in a way that each of the sequences retains its identity (e.g., linked in series) when expressed as an amino acid sequence. The heterologous polypeptides generated from the SAM RNA may then be produced as a fusion polypeptide or engineered in such a manner to result in separate polypeptide or peptide sequences.

The SAM RNA molecules described herein may be engineered to express multiple nucleotide sequences, from two or more open reading frames, thereby allowing co-expression of proteins, such as one, two or more HRV antigens (e.g. one, two or more HRV antigens) together with cytokines or other immunomodulators, which can enhance the generation of an immune response. Such a SAM RNA molecule might be particularly useful, for example, in the production of various gene products (e.g., proteins) at the same time, for example, as a bivalent or multivalent vaccine.

If desired, the SAM RNA molecules can be screened or analyzed to confirm their therapeutic and prophylactic properties using various in vitro or in vivo testing methods that are known to those of skill in the art. For example, vaccines comprising SAM RNA molecule can be tested for their effect on induction of proliferation or effector function of the particular lymphocyte type of interest, e.g., B cells, T cells, T cell lines, and T cell clones. For example, spleen cells from immunized mice can be isolated and the capacity of cytotoxic T lymphocytes to lyse autologous target cells that contain a SAM RNA molecule that encodes a HRV VP2 protein as described herein. In addition, T helper cell differentiation can be analyzed by measuring proliferation or production of TH1 (IL-2 and IFN-γ) and/or TH2 (IL-4 and IL-5) cytokines by ELISA or directly in CD4+ T cells by cytoplasmic cytokine staining and flow cytometry.

SAM RNA molecules that encode a HRV antigen, e.g. HRV peptide antigen as described herein, can also be tested for ability to induce humoral immune responses, as evidenced, for example, by induction of B cell production of antibodies specific for a HRV antigen of interest. These assays can be conducted using, for example, peripheral B lymphocytes from immunized individuals. Such assay methods are known to those of skill in the art. Other assays that can be used to characterize the SAM RNA molecules can involve detecting expression of the encoded HRV antigen by the target cells. For example, FACS can be used to detect antigen expression on the cell surface or intracellularly. Another advantage of FACS selection is that one can sort for different levels of expression; sometimes-lower expression may be desired. Other suitable method for identifying cells which express a particular antigen involve panning using monoclonal antibodies on a plate or capture using magnetic beads coated with monoclonal antibodies.

The nucleic acid-based vaccine may comprise a viral or a non-viral delivery system. The delivery system (also referred to herein as a delivery vehicle) may have adjuvant effects which enhance the immunogenicity of the encoded HRV antigen(s). For example, the nucleic acid molecule may be encapsulated in liposomes, non-toxic biodegradable polymeric microparticles or viral replicon particles (VRPs), or complexed with particles of a cationic oil-in-water emulsion. In some embodiments, the nucleic acid-based vaccine comprises a cationic nano-emulsion (CNE) delivery system or a lipid nanoparticle (LNP) delivery system. In some embodiments, the nucleic acid-based vaccine comprises a non-viral delivery system, i.e., the nucleic acid-based vaccine is substantially free of viral capsid. Alternatively, the nucleic acid-based vaccine may comprise viral replicon particles. In other embodiments, the nucleic acid-based vaccine may comprise a naked nucleic acid, such as naked RNA (e.g. mRNA), but delivery via CNEs or LNPs is preferred.

In certain embodiments, the nucleic acid-based vaccine comprises a cationic nano-emulsion (CNE) delivery system. CNE delivery systems and methods for their preparation are described in the following reference: WO2012/006380. In a CNE delivery system, the nucleic acid molecule (e.g. RNA) which encodes the antigen is complexed with a particle of a cationic oil-in-water emulsion. Cationic oil-in-water emulsions can be used to deliver negatively charged molecules, such as an RNA molecule to cells. The emulsion particles comprise an oil core and a cationic lipid. The cationic lipid can interact with the negatively charged molecule thereby anchoring the molecule to the emulsion particles. Further details of useful CNEs can be found in the following references: WO2012/006380; WO2013/006834; and WO2013/006837 (the contents of each of which are incorporated herein in their entirety).

Thus, in a nucleic acid-based vaccine of the invention, an RNA molecule encoding a HRV VP2 protein antigen may be complexed with a particle of a cationic oil-in-water emulsion. The particles typically comprise an oil core (e.g. a plant oil or squalene) that is in liquid phase at 25° C., a cationic lipid (e.g. phospholipid) and, optionally, a surfactant (e.g. sorbitan trioleate, polysorbate 80); polyethylene glycol can also be included. In some embodiments, the CNE comprises squalene and a cationic lipid, such as 1,2-dioleoyloxy-3-(trimethylammonio)propane (DOTAP). In some preferred embodiments, the delivery system is a non-viral delivery system, such as CNE, and the nucleic acid-based vaccine comprises a SAM RNA (mRNA). This may be particularly effective in eliciting humoral and cellular immune responses. Advantages also include the absence of a limiting anti-vector immune response and a lack of risk of genomic integration.

LNP delivery systems and non-toxic biodegradable polymeric microparticles, and methods for their preparation are described in the following references: WO2012/006376 (LNP and microparticle delivery systems); Geall et al. (2012) PNAS USA. Sep 4; 109(36): 14604-9 (LNP delivery system); and WO2012/006359 (microparticle delivery systems). LNPs are non-virion liposome particles in which a nucleic acid molecule (e.g. RNA) can be encapsulated. The particles can include some external RNA (e.g. on the surface of the particles), but at least half of the RNA (and ideally all of it) is encapsulated. Liposomal particles can, for example, be formed of a mixture of zwitterionic, cationic and anionic lipids which can be saturated or unsaturated, for example;

DSPC (zwitterionic, saturated), DlinDMA (cationic, unsaturated), and/or DMG (anionic, saturated). Preferred LNPs for use with the invention include an amphiphilic lipid which can form liposomes, optionally in combination with at least one cationic lipid (such as DOTAP, DSDMA, DODMA, DLinDMA, DLenDMA, etc.). A mixture of DSPC, DlinDMA, PEG-DMG and cholesterol is particularly effective. Other useful LNPs are described in the following references: WO2012/006376; WO2012/030901; WO2012/031046; WO2012/031043; WO2012/006378; WO2011/076807; WO2013/033563; WO2013/006825; WO2014/136086; WO2015/095340; WO2015/095346; WO2016/037053. In some embodiments, the LNPs are RV01 liposomes, see the following references: WO2012/006376 and Geall et al. (2012) PNAS USA. Sep 4; 109(36): 14604-9

Immunogenic Compositions

Composition comprising HRV VP2 protein or nucleic acid constructs encoding such HRV VP2 protein are also provided. The compositions may be a pharmaceutical composition, e.g. an immunogenic composition or vaccine composition. Accordingly, the composition may also comprise a pharmaceutically acceptable carrier.

A "pharmaceutically acceptable carrier" includes any carrier that does not itself induce the production of antibodies harmful to the individual receiving the composition. Suitable carriers are typically large, slowly metabolized macromolecules such as proteins, polysaccharides, polylactic acids, polyglycolic acids, polymeric amino acids, amino acid copolymers, sucrose, trehalose, lactose, and lipid aggregates (such as oil droplets or liposomes). Such carriers are well known to those of ordinary skill in the art. The compositions may also contain a pharmaceutically acceptable diluent, such as water, saline, glycerol, etc. Additionally, auxiliary substances, such as wetting or emulsifying agents, pH buffering substances, and the like, may be present. Sterile pyrogen-free, phosphate-buffered physiologic saline is a typical carrier.

Pharmaceutical compositions may include the constructs, nucleic acid sequences, and/or polypeptide sequences described elsewhere herein in plain sterile water (e.g. water for injection or "w.f.i.") or in a buffer e.g. a phosphate buffer, a Tris buffer, a borate buffer, a succinate buffer, a histidine buffer, or a citrate buffer. Buffer salts will typically be included in the 5-20 mM range. Pharmaceutical compositions may have a pH between 5.0 and 9.5 e.g. between 6.0 and 8.0. Compositions may include sodium salts (e.g. sodium chloride) to give tonicity. A concentration of 10±2 mg/mL NaCl is typical, e.g. about 9 mg/mL. Compositions may include metal ion chelators. These can prolong RNA stability by removing ions which can accelerate phosphodiester hydrolysis. Thus a composition may include one or more of EDTA, EGTA, BAPTA, pentetic acid, etc. Such chelators are typically present at between 10-500 μM e.g. 0.1 mM. A citrate salt, such as sodium citrate, can also act as a chelator, while advantageously also providing buffering activity. Pharmaceutical compositions may have an osmolality of between 200 mOsm/kg and 400 mOsm/kg, e.g. between 240-360 mOsm/kg, or between 290-310 mOsm/kg. Pharmaceutical compositions may include one or more preservatives, such as thiomersal or 2-phenoxyethanol. Mercury-free compositions are preferred, and preservative-free vaccines can be prepared. Pharmaceutical compositions may be aseptic or sterile. Pharmaceutical compositions may be non-pyrogenic e.g. containing <1 EU (endotoxin unit, a standard measure) per dose, and preferably <0.1 EU per dose. Pharmaceutical compositions may be gluten free. Pharmaceutical compositions may be prepared in unit dose form. In some embodiments a unit dose may have a volume of between 0.1-1.0 mL e.g. about 0.5 mL.

Compositions disclosed herein will generally be administered directly to a subject. Direct delivery may be accomplished by parenteral injection (e.g. subcutaneously, intraperitoneally, intravenously, intramuscularly, intradermally, or to the interstitial space of a tissue). Alternative delivery routes include rectal, oral (e.g. tablet, spray), buccal, sublingual, vaginal, topical, transdermal or transcutaneous, intranasal, ocular, aural, pulmonary or other mucosal administration. Intradermal and intramuscular administration are two preferred routes. Injection may be via a needle (e.g. a hypodermic needle), but needle-free injection may alternatively be used. A typical intramuscular dose is 0.5 ml.

A human dose or an immunologically effective amount of the protein antigen may be about or less than 50 μg of HRV VP2 protein as described herein; e.g. from 1-50 μg, such as about 1 μg, about 2.5 μg, about 5 μg, about 7.5 μg, about 10 μg, about 15 μg, about 20 μg, about 25 μg, about 30 μg, about 35 μg, about 40 μg, about 45 μg or about 50 μg. In further embodiments, a human dose of the protein antigen may be 10-50 μg or 20-50 μg. A dose of a nucleic acid (e.g. a nucleic acid-based vaccine) may vary according to the nucleic acid vector used. A human dose or immunologically effective amount of a nucleic acid may suitably be between 1 ng and 100 mg. For example, a suitable amount can be from 1 μg to 100 mg. An appropriate amount of the particular nucleic acid (e.g., vector) can readily be determined by those of skill in the art. Exemplary effective amounts of a nucleic acid component can be between 1 ng and 100 μg, such as between 1 ng and 1 μg (e.g., 100 ng-1 μg), or between 1 μg and 100 μg, such as 10 ng, 50 ng, 100 ng, 150 ng, 200 ng, 250 ng, 500 ng, 750 ng, or 1 μg. Effective amounts of a nucleic acid can also include from 1 μg to 500 μg, such as between 1 μg and 200 μg, such as between 10 and 100 μg, for example 1 μg, 2 μg, 5 μg, 10 μg, 20 μg, 50 μg, 75 μg, 100 μg, 150 μg, or 200 μg. Alternatively, an exemplary effective amount of a nucleic acid can be between 100 μg and 1 mg, such as from 100 μg to 500 μg, for example, 100 μg, 150 μg, 200 μg, 250 μg, 300 μg, 400 μg, 500 μg, 600 μg, 700 μg, 800 μg, 900 μg or 1 mg.

Generally a human dose will be in a volume of between 0.1 ml and 2 ml, typically between 0.2 and 1 ml, such as 0.5 or 0.625 ml. Thus the composition described herein can be formulated in a volume of, for example, about 0.1, 0.15, 0.2, 0.5, 1.0, 1.5 or 2.0 ml human dose per individual or combined immunogenic components. In a particular embodiment a human dose is contained in 0.5 ml of the composition.

For any component of the immunogenic compositions disclosed herein, the dosage can vary with the condition, sex, age and weight of the targeted subject or population and the administration route of the immunogenic composition or vaccine.

Human Rhinoviruses are the primary cause of acute upper respiratory tract infections in humans, known as the common cold. They are also the most common viral cause of severe exacerbation of chronic respiratory diseases such as asthma and chronic obstructive pulmonary disease (COPD). The inventors found that using compositions of the invention (i.e. comprising a VP2 protein antigen), optionally adjuvanted, an immune response can be generated which partially or fully protects the subject against subsequent infections and/or disease by the same or another HRV types, the immune response thus being cross-reactive. The inventors also found the immune response generated to be at least cell-mediated. In a further embodiment, also cross reactive antibodies are induced, that may or may not be neutralizing.

In some embodiments, the compositions disclosed herein are for use in a subject to: prevent HRV infection (prophylactic use), reduce HRV viral infection load, reduce recovery time, and/or lower disease severity caused by a HRV in that subject. The term "recovery time" refers to reducing the time for recovery from an infection by HRV. Alternatively, the compositions are for use in a method to reduce or prevent disease in a subject, i.e. reduce or prevent the clinical symptoms upon HRV infection, e.g. by reducing the severity of exacerbations in a patient diagnosed with asthma or COPD.

One of ordinary skill in the art will understand that prevention or prophylactic use of the compositions disclosed herein are not meant to imply 100% effectiveness in any given population. Rather, there are varying degrees of prevention or prophylaxis which one of ordinary skill in the art recognizes as having beneficial effect(s). In this respect, the inventive methods can provide any level of prevention or prophylaxis. Compositions described herein and their use may simultaneously prevent or reduce HRV infection and HRV related clinical symptoms such as asthma or COPD exacerbations.

In some embodiments, the compositions disclosed herein are for use in a method for inducing a (cross-reactive) immune response against HRVs of at least three different serotypes. The immune response generated upon administering a subject a composition comprising a VP2 protein derived from an HRV type belonging to HRV-A may be cross-reactive against challenge of the subject with an HRV type belonging to HRV-A, HRV-B and/or HRV-C. Similarly, the immune response generated upon administering a subject a composition comprising a VP2 protein derived from an HRV serotype belonging to HRV-B may be cross-reactive against challenge of the subject with an HRV type belonging to HRV-B, HRV-A and/or HRV-C, or, the immune response generated upon administering a subject a composition comprising a VP2 protein derived from an HRV type belonging to HRV-C may be cross-reactive against challenge of the subject with an HRV type belonging to HRV-A and/or HRV-B.

In further embodiments of the uses and methods disclosed herein, the target population for the uses or methods disclosed herein are human patients diagnosed with COPD or asthma. The target population may be limited to human COPD patients.

In some embodiments, methods are provided for preventing HRV viral infection, reducing HRV viral infection load, and/or reducing or preventing the clinical symptoms of HRV infection in a human subject in need thereof, which comprises administering to said subject an immunologically effective amount of any of the immunogenic compositions as provided herein.

In some embodiments, methods are provided for inducing a cross-reactive immune response against at least three types of HRV in a human subject in need thereof, which comprises administering to said subject an immunologically effective amount of any of the immunogenic compositions as provided herein.

In some embodiments is provided use of a HRV VP2 protein as disclosed herein in the manufacture of an immunogenic composition for preventing or reducing the duration of HRV infection in a human subject, and/or reducing or preventing the clinical symptoms of HRV infection in a human subject.

In some embodiments is provided use of a HRV VP2 protein as disclosed herein in the manufacture of an immunogenic composition inducing a cross-reactive immune response against at least three serotypes of HRV in a human subject in need thereof.

In some embodiments, subject is a human subject. In specific embodiments, the human subject is an asthma patient, or, the human subject is a COPD patient.

In some embodiments, the human subject is a subject young in age such as an infant, toddler or child. In further embodiments the human subject is an infant, toddler or child that is an asthma patient. In some embodiments, the human subject is an elderly subject, e.g. 50 years of age (yoa) or older, 60 years of age (yoa) or older, or, 70 years of age (yoa) or older. In further embodiments the human subject is an elderly subject that is a COPD patient. In those embodiments, the target population is defined accordingly.

The following examples illustrate the invention.

EXAMPLES

Example 1

The objective of the experiment was to compare the quality, diversity and the magnitude of neutralizing antibodies induced pre/post intranasal HRV1b challenge in mice primed with AS01b adjuvanted combination of VP2 and VP4 proteins compared to mice primed with AS01b adjuvanted VP4 proteins or AS01b alone.

1.1 Animal Model

CB6/F1 mouse strains were chosen to study the immunogenicity of HRV vaccine candidates since these animals are able to mimic both humoral and cellular immune responses induced upon natural HRV infections. Moreover, CB6/F1 mice are able to recapitulate virological & histological signs observed in humans (neutrophils recruitment and cytokine production in lungs) when challenging with HRVs belonging to minor group (replicative in mice).

1.2 Experimental Design

In this study, 3 groups of CB6/F1 mice (n=30/group) were intramuscularly immunized twice (in the gastrocnemius muscle) on days 0 & 14 (D0 and D14) with 5 µg of:

GROUP 1—A combination of HRV39 VP2 (SEQ ID NO:1)+concatemer of full length VP4 Glade A proteins (SEQ ID NO: 3; VP4 proteins specific for HRV2, 8, 10, 21, 39, 60, 71, 77, CU107 & CU150 types) formulated in AS01b.

GROUP 2—Concatemer of full length VP4 Glade A proteins (SEQ ID NO: 3; VP4 proteins specific for HRV2, 8, 10, 21, 39, 61, 77, CU107 & CU150 types) formulated in AS01b GROUP 3—AS01b alone as negative control.

AS01b comprises 3D-MPL and QS21 in cholesterol-containing liposomes. One Human Dose (HD) of AS01b contains 50 µg MPL, 50 µg QS21, in cholesterol-containing liposomes.

Four weeks later (D42), mice were intranasally challenged with $10^6$TCID50 units of purified HRV1b virus and the levels of cross-reactive CD4+/CD8+ T cell responses and the quality, diversity and the magnitude of neutralizing antibodies were investigated in serum samples and spleen cells collected at days 14 post second immunization (pre-challenge) and days 14 post-HRV1b challenge.

The levels of single-stranded positive RNA genomes, cytokines production (MCP-1, IL-6, IL-10, IL-12p70, TNF-α, INF-γ) and cell differential counts were investigated in bronchoalveolar lavage (BAL) fluids at day 2 post-HRV1b challenge (D44) in order to ensure that HRV1b challenge was successfully achieved. The complete description for each group and immunization schedule is referred to in Table 2.

TABLE 2

| Group | N | Immunogen (5 μg/immunogen/dose) | Priming Adjuvant dose (AS01b) | Immunization schedule | Intranasal challenge schedule ($10^6$ TCID50 units) |
|---|---|---|---|---|---|
| 1 | 30 | HRV39 VP2 protein (SEQ ID NO: 1) + concatemer of VP4 clade A proteins (SEQ ID NO: 3) | 1/10 HD | Days 0, 14 | Day 42 |
| 2 | 30 | Concatemer of VP4 proteins (SEQ ID NO: 3) | 1/10 HD | Days 0, 14 | |
| 3 | 30 | None | 1/10 HD | Days 0, 14 | |

N: Number of mice per group;
HD = Human dose;
NA = not applicable.

1.3 Material—Antigens and Adjuvants

The antigens used in this experiment were produced as follow:
The HRV39 VP2 protein (SEQ ID NO: 1 with C-terminal His tag sequence GGHHHHHH) was expressed in *Pichia* (yeast) system and purified from a CsCl density gradient centrifugation followed by a size exclusion chromatography on a Sephacryl S-500 HR/concentration on Amicon and dialysis. The concatemer of full length Clade A VP4 proteins (SEQ ID NO: 3) was expressed in *E. coli* (BL21). The purification was performed using a Ni-NTA GE His trap column followed by a size exclusion chromatography on a Superdex75 using 25 mM Bicine-4 M urea buffer (4 M urea-25 mM Bicine-500 mM NaCl, 1% sucrose-0.1% pluronic F68, pH8.0). Material was finally dialysed into PBS buffer supplemented with 1% empigen.

All antigens were formulated with the adjuvant AS01b (1/10 HD).

Highly purified HRV1b viral material used for the IN challenge was purchased from Virapur Laboratories (VIRAPUR, San Diego, Calif. USA).

Example 2: Methods 2.1 Rhinovirus Neutralization Assay

Quantitation of neutralizing antibodies was performed using the following neutralization assay. A suspension of 5000 H1-HeLa cells/well was seeded in flat-bottom 96-well plates (Nunclon Delta Surface, Nunc, Denmark) and incubated overnight at 37° C. with 5% $CO_2$.

Sera were diluted by 2-fold serial dilution (starting at 1/10) in HRV infection medium (MEM supplemented with 2% FCS, 30 mM $MgCl_2$, 2 mM L-glutamine, 1% non-essential amino acids and 1% penicillin/streptomycin) in 96-well plates (Nunc, Denmark) and incubated with a concentration of 100 $TCID_{50}$ of virus for 2 h at 37° C. (5% $CO_2$). Edges of the plates were not used and one column of each plate was left without sera and was used as the negative control (no neutralization). Medium of the 96 well plates seeded with H1-HeLa cells was decanted and the virus-antibody mixtures were then overlaid on subconfluent H1-HeLa cells and incubated at 34° C. with 5% $CO_2$ for 72 hours or 120 hours (depending on HRV strains used—see table 3).

TABLE 3

| Three days of infection (72 h) | Five days of infection (120 h) |
|---|---|
| HRV1b, 2, 3, 8, 14, 16, 28, 39 | HRV25, 29. |

Three or five days post-infection, H1-HeLa cells were washed and incubated at 37° C. for 8 h (5% $CO_2$) with a WST-1 solution (reagent for measuring cell viability) diluted 15×(Roche, 1164807001, lot number 12797000) in HRV revelation medium (DMEM supplemented with 2% FCS, 30 mM $MgCl_2$, 2 mM L-glutamine, 1 mM sodium-pyruvate, 50 μM β-mercaptoethanol, 1% non-essential amino acids and 1% penicillin/streptomycin). The plates are then read at 450 nm wavelength using Softmaxpro Software.

To calculate neutralizing antibody titers, sets of data were normalized based on the mean of WST-1 O.D. in "cells w/o virus" wells and "cells w/o serum" wells to 0 and 100% cythopathic effect (CPE) respectively. Percentage of inhibition of CPE at a dilution i was then given by:

% inhibition=$(O.D._i$–Mean $O.D._{cells\ w/o\ serum})$/(Mean $O.D._{cells\ w/o\ virus}$–Mean $O.D._{cells\ w/o\ serum})$ The reciprocal of the dilution giving a 50% reduction of CPE was then extrapolated using non-linear regression.

2.2 Measurement of Rhinovirus-specific CD4+/CD8+ T-cells by Intracellular Cytokine Staining.

The frequencies of antigen-specific CD4+ & CD8+ T-cells producing IL-2, IFN-γ and/or TNF-α were evaluated by intracellular cytokines staining (ICS) in spleen collected on (a) day 14 post $2^{nd}$ immunization (D28 pre-challenge), and (b) on days 14 post HRV1b challenge (D56 post $2^{nd}$ immunization).

Isolation of Splenocytes

Spleen were collected in RPMI 1640 medium w/o L-glutamine supplemented with RPMI additives (=RPMI medium) and dissociated in a single-cell suspension which was transferred on a 100 μm cell strainer and rinsed with 5 ml of the RPMI medium. Spleen cells were then centrifuged at 335 g for 10 min (4° C.) and pellet was resuspended in 5 ml of RPMI medium. This previous washing step was repeated one more time and the final pellet was resuspended in 5 ml of RPMI medium supplemented with 5% FCS.

Cell suspension was then diluted 20× (10 μl) in PBS buffer (190 μl) for cell counting (using MACSQuant Analyzer). After counting, cells were centrifuged again (335 g, 10 min, RT) and the cell pellet was resuspended at $10^7$ cells/ml in RPMI medium.

Cell Preparation

Splenocytes were seeded in round bottom 96-well plates at approximately 1 million cells per well. Splenocytes were stimulated in-vitro with 100 μl of:
  a pool of 15 mer peptides overlapping by 11aa covering the whole amino acids sequence of VP2, VP4 proteins from HRV2, 14 & 39 strains at working concentration of 1 μg/ml per peptide.

ultra centrifuged (UC) HRV3 & 28 particles at 1.4× $10^7$ TCID$_{50}$/ml (~MOI 1).

UC HRV25 particles at 1.4×$10^6$ TCID$_{50}$/ml (~MOI 0.1).

UC uninfected cell lysate or medium (as negative controls of the assay).

PMA—ionomycin solution at working concentrations to 0.25 μg/ml & 2.5 μg/ml respectively (as positive control of the assay).

CD4 T 49d and CD28 antibodies (1 μg/ml) were added and cells were incubated for:

2 h at 37° C. followed by 4 h in presence of brefeldin (1 μg/ml) to inhibit cytokine secretion for in-vitro stimulation using the pools of peptides from VP2, VP4 proteins from HRV2, 14 & 39 strains.

16 h at 37° C. followed by 4 h in presence of brefeldin (1 μg/ml) to inhibit cytokine secretion for in-vitro stimulation using UC viral preparations (HRV3-25-28).

Intracellular Cytokine Staining (ICS)

Cell staining was performed as follows: cell suspensions were placed in v-bottom 96 well plates, pelleted (150 g, 5 min at 4° C.), and washed in 250 μl PBS 1% FCS. Cells were pelleted again and resuspended in 50 μl of PBS 1% FCS containing 2% Fc blocking reagent (1/50; CD$^{16}$/32). After 10 min incubation at 4° C., 50 μl of a mixture of anti-CD4 T-V450 (1/200), anti-CD8 T perCp-cy 5.5 (1/100) and Live & Dead PO (1/1000) was added and incubated 30 min in obscurity at 4° C. After a washing in PBS 1% FCS, cells were permeabilized in 200 μl of Cytofix-Cytoperm (Kit BD) and incubated 20 min at 4° C.

Cells were then washed with Perm Wash (Kit BD) and resuspended with 50 μl of anti-IFNg APC (1/200)+anti-IL-2 FITC (1/400)+anti-TNFα PE (1/700) diluted in PermWash. After 1 h incubation at 4° C., cells were washed with Perm Wash and resuspended in 220 μl PBS.

Cell Acquisition and Analysis

Stained cells were analyzed by flow cytometry using a LSRII and the FlowJo software. Live cells were identified with the Live/Dead staining and then gated with FSC/SSC and acquisition was performed on ~20,000 events (CD4+ T-cells). The percentages of IFN-γ+/IL-2++/− TNFα producing cells were calculated on CD4 T + and CD8 T + gated populations.

List of reagents used (reference numbers as available at the time of filing)

| Reagents | Catalog No. | Lot numbers | Suppliers |
|---|---|---|---|
| RPMI 1640 medium | 31870-025 | 1683050/1734648 | Gibco |
| RPMI additives | SR120 | D16R001083 | In house |
| PBS Ca$^{++}$ & MG$^{++}$ free | BE17512Q | 5MB165 | Lonza |
| Inactivated Foetal Calf Serum | FBS-HI-12A | CP15-1084 | Capricorn |
| anti-mouse CD16/32 | 553142 | 5154726 | BD |
| anti-mouse CD4 V450 | 560468 | 5065793 | BD |
| anti-mouse CD8 PerCp Cy 5.5 | 551162 | 5156801 | BD |
| Live & Dead PO | L34959 | 1733112 | Molecular Probes |
| Cytofix/Cytoperm | 51-2090K2 | 5075560 | BD |
| Permwash 10x cc | 554723 | 4198590 | BD |
| anti-mouse IL-2 FITC | 554427 | 4344599 | BD |
| anti-mouse IFN-g APC | 554413 | 4226904 | BD |
| anti-mouse TNF-a PE | 554419 | 3018857 | BD |
| anti-mouse CD28 | 553294 | 83839 | BD |
| anti-mouse CD49d | 553313 | 4105875 | BD |
| Phorbol Myristate Acetate (PMA) | P8139-1MG | MKBS5634V | Sigma |
| Ionomycin | I0634-1MG | RNBD5728 | Sigma |
| Golgi plug (Brefeldin) | 555029 | 4309737 | BD |
| EPI | LOG081D | D16R001486 | In house |
| CS&T calibration beads | | 94851 | BD |

2.3 Differential Cell Counts in BAL fluids.

The frequencies of leukocytes recovered in BALs at day 2 post-HRV1b challenge were evaluated by immune cell phenotyping using flow cytometry. A panel of fluorochrome-conjugated antibodies specific for Ly6C-FITC, SiglecF-PE, Ly6G-PerCP, CD11-PB, CD3-APC-Cy7, CD11C PE-Cy7 was used in order to easily discriminate macrophages (CD11c+/CD11b−/SiglecF+), monocytes (CD11c−/CD11b+/Ly6c+/Ly6g−), eosinophils (CD11b+/CD11c−/SiglecF+), neutrophils (CD11c−/CD11b+/Ly6c+/Ly6g+) and lymphocytes (CD11c−/CD11b−/CD3+).

Mice were sacrificed and lungs were washed and massaged gently 3 times with 500 μl of PBS −5 mM EDTA. The recovered fluid was then centrifuged (1000 g-10 min-25° C.), and used for CBAflex & HRV1b-specific qRT-PCR assays while cell pellet was resuspended in PBS—2 mM EDTA (supplemented with 2% FCS) and cells were seeded in a 96-well polypropylene (depending on number of cells recovered—from 7.2 $10^3$ to 1.2×$10^5$ cells/well).

The plates were then washed with PBS+2 mM EDTA+2% FCS and centrifuged (1000 g-5 min-4° C.). Supernatant was removed and pellet was resuspended in 25 μl of blocking RFc (Rat anti-mouse CD16/CD32 (2.4 G2), (ref: 553142, lot number 4198965) prediluted 1/50 in PBS+2 mM EDTA+2% FCS and incubated for 10 min at 4° C.

25 μl of a mix of fluorochrome-conjugated antibodies diluted as follows: Ly6C-FITC(1/200) (ref:553104, lot number: 4330779) SiglecF-PE(1/150) (ref:552126, lot number: 3277625), Ly6G-PerCP(1/100) (ref:560602, lot number: 5188651), CD11$_b$-PB(1/300) (ref:RM2828, lot number: 1642766), CD3-APC-Cy7(1/100) (ref:100222, lot number: B199708), CD11$_c$-PE-Cy7(1/400) (ref:558079, lot number: 4286714) was then added for 30 min at 4° C. The plates were then centrifuged (1000 g-5 min-4° C.), and pellet was resuspended in PBS, and sample analysis was performed by flow cytometry. Live cells were gated (FSC/SSC) and acquisition was performed on ~100,000 events.

2.4 Quantification of Secreted Cytokines in BAL Fluids (CBA Flex Assay)

Quantification of secreted cytokines (IL-6, TNF-α, INF-γ, IL-12p-70, IL-10, MCP-1) in BAL fluids collected at day 2 post-HRV1b challenge was also performed using BD™ Cytometric Bead Array (CBA, BD, USA—ref 552364; lot number 5261593) following manufacturer's instructions on undiluted samples.

FACS instrument setup procedures were performed using performance check (using CS&T beads) and daily cleaning protocol. Standards were reconstituted in Assay Diluent (stock concentration at 50000 pg/ml), allowed to equilibrate to room temperature for at least 15 min, mixed and 2-fold serial dilutions were performed starting dilution from 5000 pg/ml up to 5 pg/ml.

In 96-well plate, 50 μL of mixed standard curve or undiluted samples were added to the appropriate assay wells & 50 μL/well of mixed capture beads (IL6, TNF-α, INF-γ, IL-12p-70, IL-10, MCP-1) were added to each assay well. The plates were mixed for 5 minutes using a digital shaker. Plates were then incubated for 1 hour at room temperature, protected from light.

50 µL/well of the mixed PE detection reagent were added to each well and mixed for 5 minutes using the digital shaker. Plates were incubated again for 1 hour at room temperature, protected from light.

The plates were centrifuged at 1000 rpm for 5 min (with brake), supernatant was carefully removed using a multi-channel pipet and the beads were resuspended in 200 µL of wash buffer.

Samples were then acquired by FACS (Fortessa) and analyzed using the Flowjo software (FCAP Array).

2.5 Detection of Single Stranded Positive RNA Genomes in BAL Fluids

In order to ensure that mice were successfully challenged with HRV1b strain, the levels of single stranded positive HRV1b genomic RNA were investigated in BAL fluids collected at day 2 post-HRV1b challenge. BAL samples were centrifuged (1000 g-10 min-25° C.) and supernatant was used to detect/quantify genomic RNA (positive stand) by qRT-PCR assay. RNA was purified from 100 µl BAL sample (50 µl BAL/50 µl RNA later) using QIAamp Viral RNA mini kit (Qiagen) 2, 6 or 14 days post inoculation.

Genomic (positive strand) RNA was detected as follows: Reverse transcription: RNA, random primer and dNTP were heated for 10 min at 65° C. and then placed on ice. cDNA was synthetized with Superscript III reverse transcriptase for 50 min at 55° C. and then heat inactivated at 70° C. for 15 min.

Real-time PCR was carried out on 2 µl cDNA with 900 nM forward primer (RV-F1), 300 nM reverse primer (RV-R1) and 200 nM of probe (RV-Probe) using TAQMAN Gene Expression Master Mix. The cycling conditions of qPCR were: 2 min at 50° C., 10 min at 95° C., followed by 45 cycles of 15 sec at 95° C. and 1 min at 60° C.

Example 3: Results 3.1 Quantification of Single Stranded Positive RNA Genome

The following results were obtained:

High levels of positive RNA genomes (~$10^7/10^8$ RNA copy number/ml BALs) were detected in BAL fluids of challenged mice, attesting that IN HRV1b challenge was successfully achieved (FIG. 1).

The ability of virus particles to replicate was not investigated due to poor level of negative strand expressed in BAL fluids.

3.2 Whole Blood Differential Counts

Figure 2:
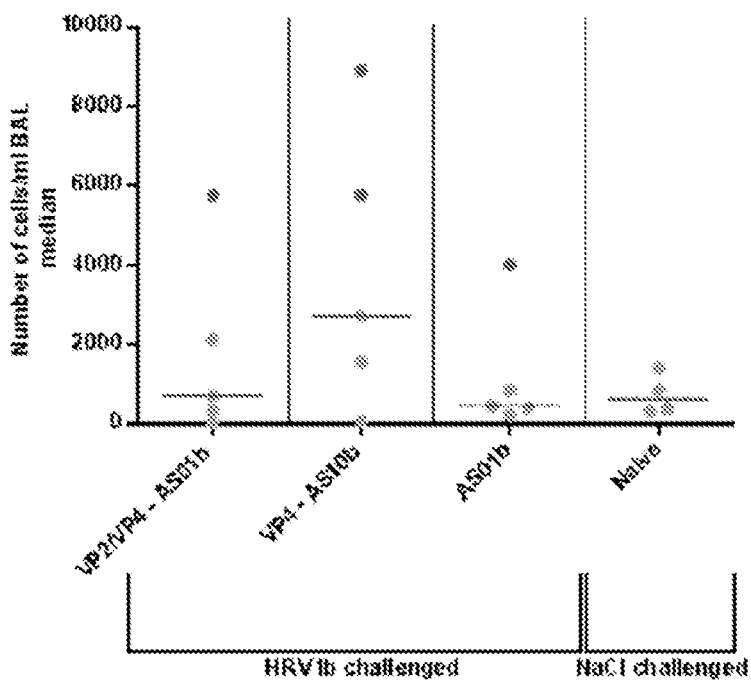

The inflammatory immune response was investigated by counting the number of whole blood cells (lymphocytes, neutrophils, macrophages, eosinophils) recovered in BAL fluids at day 2 post-HRV1b challenge. The following results were obtained:

Two to five times higher levels of neutrophils (2000-9000 cells/ml BAL) was detected in some mice challenged with HRV1b strain compared to mice challenged with NaCl 150 mM (exp 20140293-<2000 cells/ml BAL) (FIG. 2), suggesting that HRV1b challenge induces neutrophil infiltration. However, it is important to highlight that the levels of neutrophils detected in BAL fluids post-challenge are variable from one mouse to another.

Figure 3:
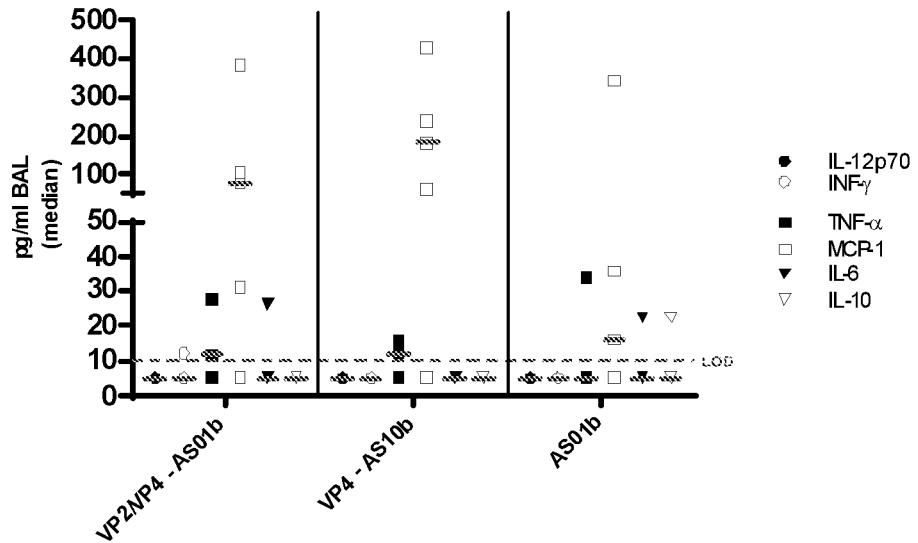

3.3 Quantification of Secreted Cytokines/Chemokines in BAL Fluids Using CBA Flex Assay Measurement of protein levels of 6 inflammatory cytokines (TNF-α, INF-γ, IL-6, IL-10 & IL-12p70) & chemokines (MCP-1) was performed by CBAflex assay in BAL fluids collected at day 2 post-HRV1b challenge. The following results were obtained:

High level of pro-inflammatory MCP-1 chemokines (>20 pg/ml) was detected in some of BAL fluids of some challenged mice (FIG. 3). It is also important to highlight that the induction of MCP-1 chemokines was variable from mice to another & within the same group.

No or limited levels of INF-γ, TNF-α IL-6, IL-10, IL-12p-70-type cytokines were detected in BAL fluids (FIG. 3).

3.4 Rhinovirus-specific CD4/CD8+ T-cell Responses Detected in Spleen Cells Collected Pre & Post HRV1b Challenge The levels of HRV-specific CD4+/CD8+ T cell responses were investigated in spleen cells collected at days 14 post second immunization (pre-challenge) and days 14 post-HRV1b challenge.

Type-specific CD4+/CD8+ T cell responses were investigated using a pool of peptides covering the whole sequence of VP2 (from HRV39) or VP4 (from HRV2 & 39 serotypes) proteins while cross-reactive CD4+/CD8+ T cell responses were investigated using either a pool of HRV2 or HRV14-derived peptides covering the whole sequence of VP2 or VP4 proteins, or ultracentrifuged (UC) HRV3, 25 or 28 particles (multiplicity of infection (MOI) 0.1-1 depending on HRV strains used). The following results were obtained.

Type-specific CD4+ T-cell Responses

Figure 4:
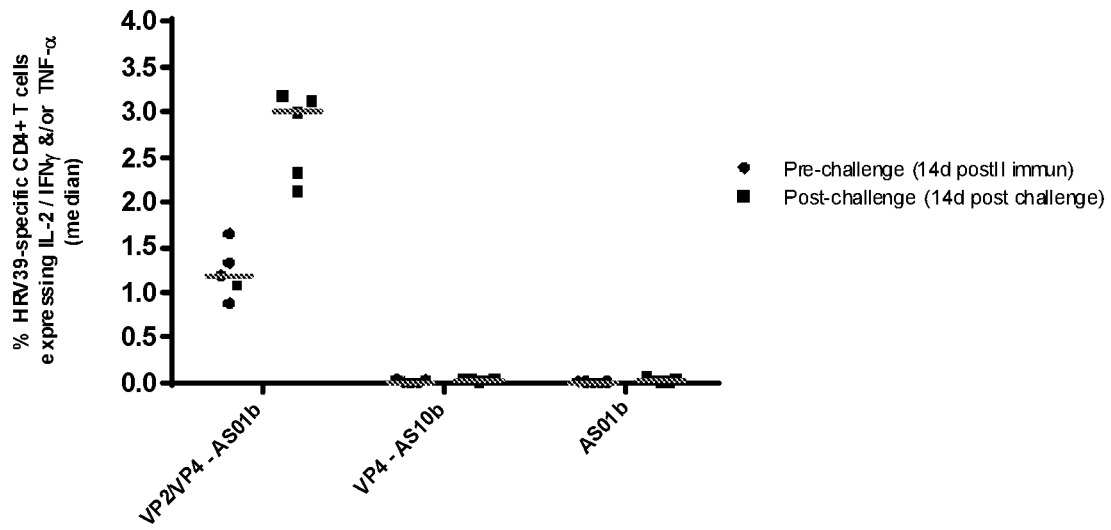

High frequency (0.8-1.7%) of HRV39 VP2-specific CD4+ T cell responses was detected pre-HRV1b challenge in group 1 (VP2/VP4) but not in the other groups. Interestingly, this response was boosted (~2-fold more higher) 14 days post-HRV1b challenge (1.7 3.2%) in group 1 (FIG. 4).

Figure 5:
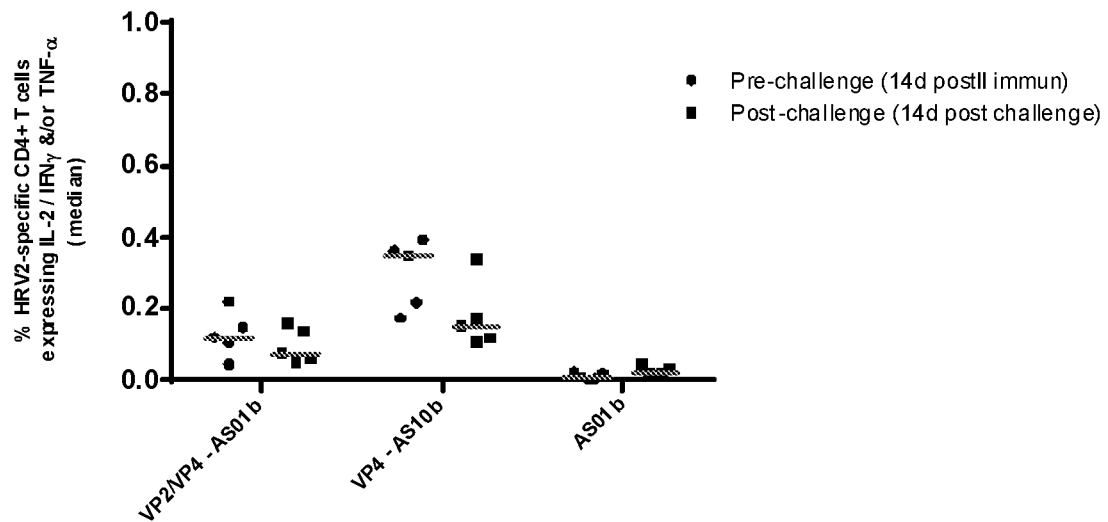
Figure 6:
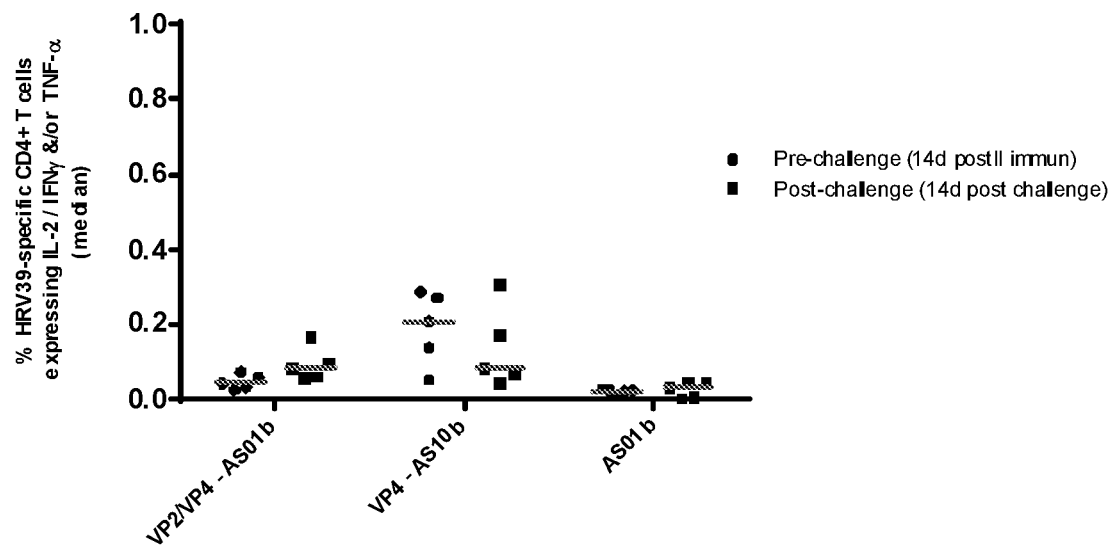

No or low frequency (0.1-0.5%) of HRV2/39 VP4-specific CD4+ T cell responses was detected in all groups. No boost effect was detected 14 days post-HRV1b challenge (FIGS. 5 and 6).

Cross-reactive CD4+ T-cell Responses

No cross-reactive CD4+ T cell response against HRV14 (cladeB) VP4 protein was detected pre/post HRV1b challenge (data not shown).

Figure 7:
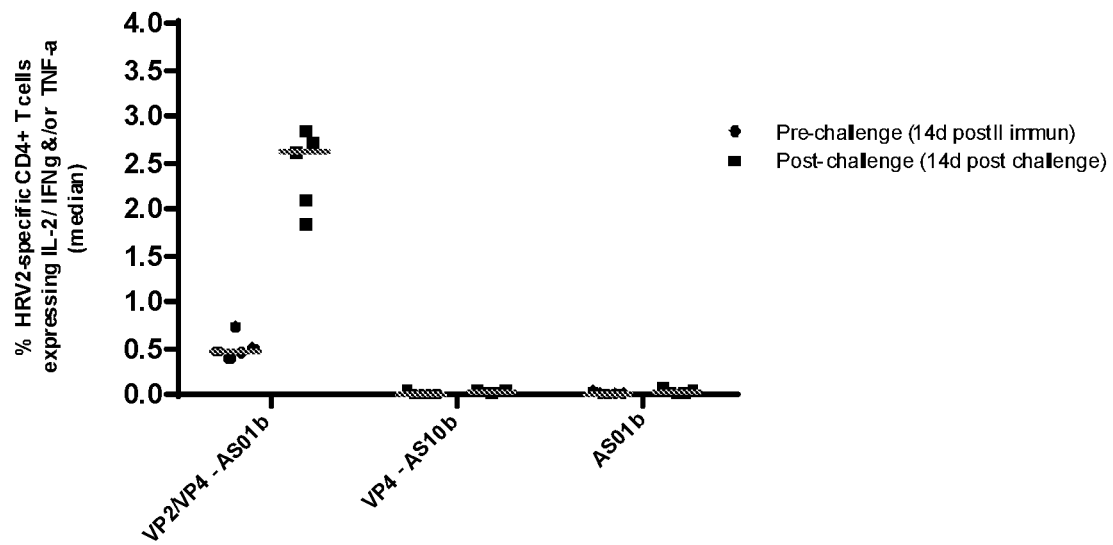
Figure 8:
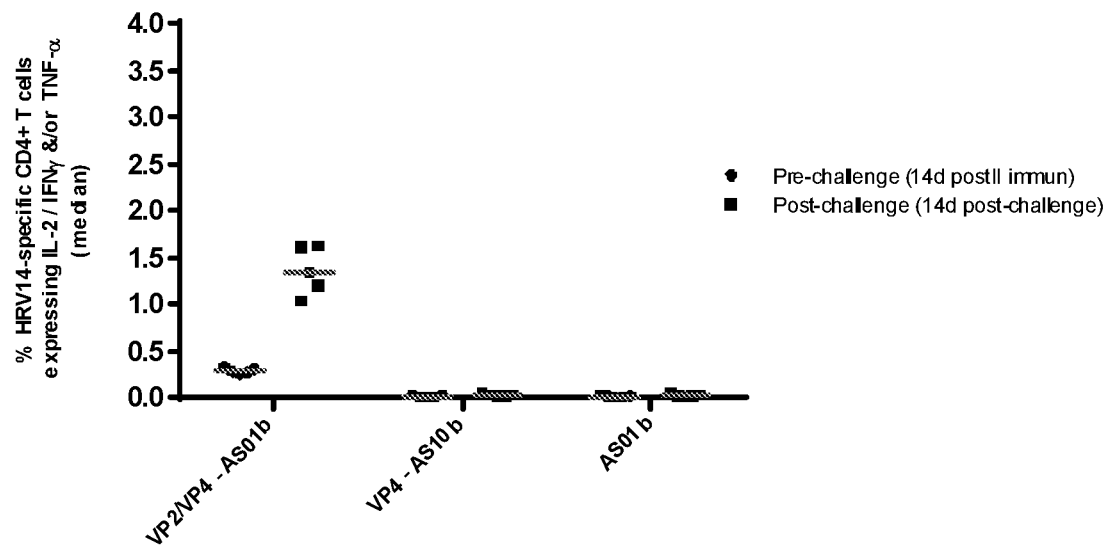

Cross-reactive CD4+ T cell responses against VP2 from HRV2 (cladeA/m) or HRV14 (cladeB) were already detected pre-HRV1b challenge in group 1(frequency range 0.2-0.8%) but not in other groups. As for the specific CD4+ T cell response, the cross-reactive VP2 responses were also boosted (~4-fold more higher) 14 days post HRV1b challenge (1.0-2.9%) (FIGS. 7 and 8).

Cross-reactive CD4+ T cells against HRV25 particles (cladeA/m) was already detected pre-HRV1b challenge in group 1 (frequency range 0.5-1.5%) of but not in the other groups. A boost effect of the response was detected 14 days post-HRV1b-challenge (FIG. 9).

No or low levels of cross-reactive CD4+ T cells (<0.2%) against HRV3 (cladeB) & 28 (cladeA/M) particles were detected pre HRV1b-challenge. CD4+ T cell responses against HRV3 (0.25-0.5%) or HRV28 strain (0.35-1%) were boosted 14 days post-HRV1b challenge in group 1 but not in the other groups (FIGS. 10 and 11).

CD8+ T-cell Responses

No CD8+ T cell responses were detected pre/post HRV1b challenge following in-vitro stimulations with HRV2/14/39 VP2/VP4-derived peptides or UC HRV3 & 28 particles (data not shown).

HRV25-specific CD8+ T cell responses were detected pre HRV1b challenge in group 1 and group 2. The frequency of this CD8+ T cell response was boosted 14 days post-HRV1b-challenge (0.4-1%) but only in group 1 (FIG. 12).

3.5 Measurement of HRV-specific Neutralizing Antibody Responses in Serum Samples Collected Pre/Post HRV1b Challenge The levels of HRV-specific neutralizing antibodies were investigated in pooled mice sera (5 or 7 pools of 3 mice/gr) collected 14 days post second immunization (pre-challenge) or 14 days post-HRV1b challenge. The neutralizing activity was tested against the following strains:

CladeA/m: HRV1b, 2, 25, 29
CladeA/M: HRV8, 16, 28, 39
CladeB: HRV3 & 14

The following results were obtained:
No neutralizing antibodies (nAbs) against HRV2, 3, 8, 14, 16, 25, 28, 29, 39 strains were detected pre & post HRV1b challenge (data not shown).
higher levels of nAbs specific for the challenging serotype virus (HRV1b) were detected days 14 post-challenge in sera from mice of group 1 compared to other groups (GMR of 13.00 between gr1 & 2, GMR of 6.99 between gr 1 & 3) (FIG. 13). This indicates that priming with HRV39 VP2 protein enhances the generation of nAbs to infection with the heterosubtypic strain (HRV1b).

Example 4: Mouse Immunogenicity Study

A mouse immunogenicity study was initiated with recombinant HRV39 VP0, VP2, or VP4 protein, adjuvanted with AS01B. The primary objective of this study was to demonstrate homologous and heterologous antigen-specific T-cell responses in mice vaccinated with recombinant HRV39 VP0, VP2 or VP4 protein using an intracellular cytokine staining assay.

4.1 Materials and Methods:

Five groups of female CB6F1 mice (6-8 weeks old) were immunized on days 0 and 28 by intramuscular injection with either saline (control), recombinant HRV39 VP0 adjuvanted with AS01B, HRV39 VP2 adjuvanted with AS01B, HRV39 VP4 protein adjuvanted with AS01B, or HRV39 live virus (Virapur).

On day 42, serum was generated from all mice for serological testing and spleens were harvested from 6 mice per group for immunogenicity testing by intracellular cytokine staining. Splenocytes were incubated overnight with peptide pools (15-mers with 11 amino acid overlaps) of VP2 or VP4 from five HRV types (HRV39, HRV1b, HRV2, HRV14, and HRV89) followed by a 4-hour incubation with brefeldin A. Cells were stained for viability, fixed, permeabilized, and then stained with fluorescently labeled antibodies against CD3, CD4, CD8, CD44, IFN-γ, TNF-α, IL-2, CD107a, IL-13, IL-4, IL-17A, and IL-17F. Data was acquired using a BD Fortessa flow cytometer and analyzed using FLOWJO X prior to being graphed in GraphPad Prism.

Remaining mice were immunized intranasally with live HRV1b virus, with the exception of the control group treated with saline, on day 56. Spleens and serum will be collected on study day 70 for further immunological testing.

Figure 14A:
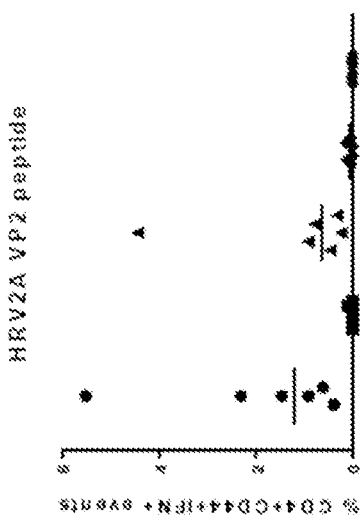
Figure 14B:
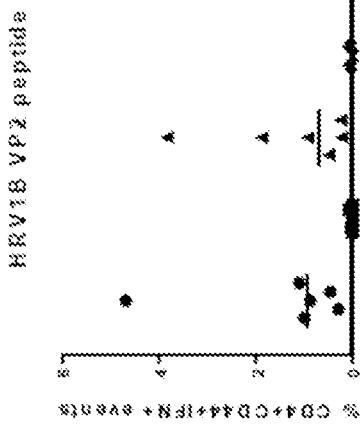
Figure 14C:
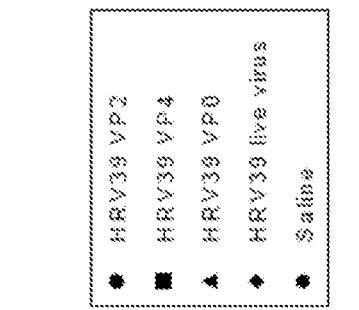
Figure 14D:
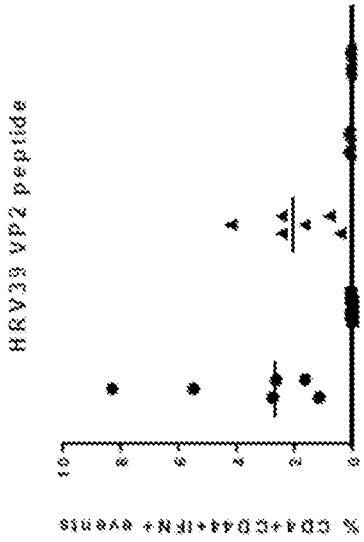
Figure 14E:
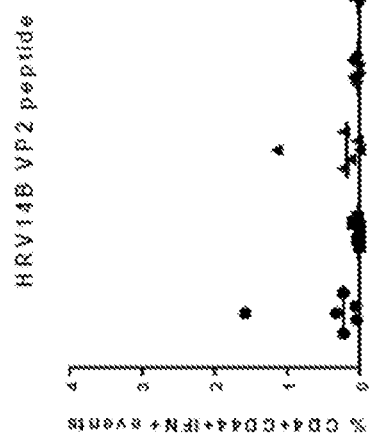
Figure 15C:
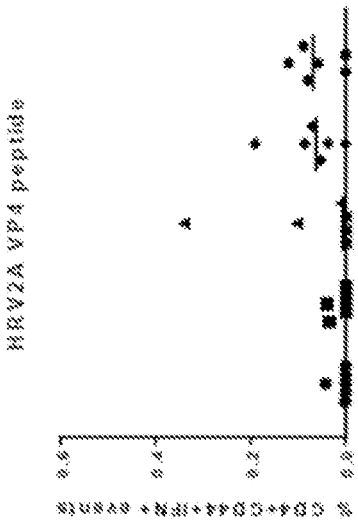
Figure 15B:
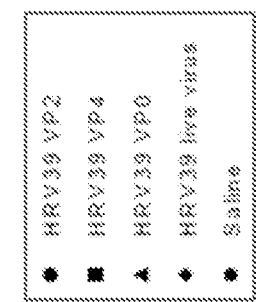
Figure 15B:
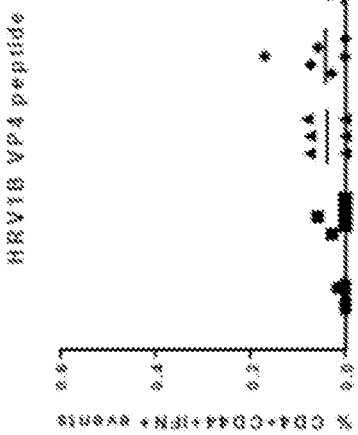
Figure 15A:
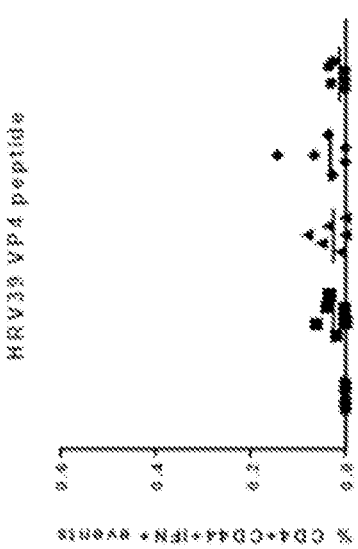
Figure 15E:
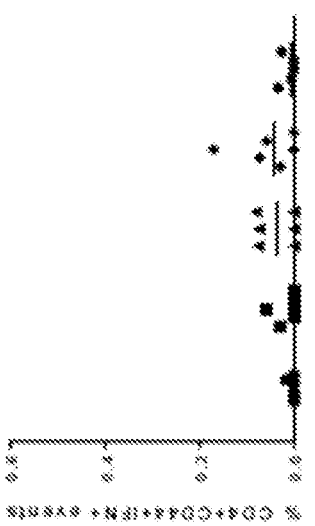
Figure 15D:
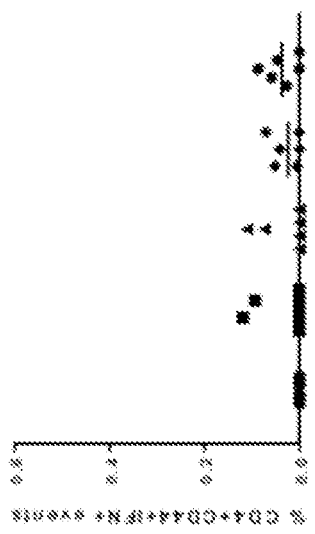

4.2 Results:

In splenocytes collected on day 42, antigen-specific CD4+ T-cell responses were detected in the mice immunized with HRV39 VP2 or VP0 as described in 4.1, above, in response to stimulation with a homologous VP2 peptide pool from HRV39 (FIG. 14A) and with heterologous VP2 peptide pools from HRV1B (FIG. 14B), HRV2 (FIG. 14C), HRV89 (FIG. 14D) and HRV14 (FIG. 14E). In FIGS. 14A-14E, data displayed are individual mice (n=6 per group) with the median indicated by a horizontal line. Moving from left to right in each of FIG. 14A-14E, the columns show data from mice immunized with HRV39 VP2 (circle), HRV39 VP4 (square), HRV39 VP0 (triangle), HRV39 live virus (diamond), and saline (hexagon), respectively. Note the differences in upper limit on Y-axis.

Splenocytes from HRV39 VP4 immunized mice produced little to no IFN-γ in response to stimulation to homologous (HRV39) or heterologous (HRV1B, HRV2, HRV89, or HRV14) VP2 peptide pool stimulation (FIG. 15). Little to no CD8+ antigen-specific T-cell responses were detected to homologous or heterologous peptide pool stimulations (data not shown).

Little to no IFN-γ was produced by CD4+CD44+ T-cells from splenocytes of mice immunized with HRV39 VP2, VP4 or VP0 in response to stimulation with VP4 peptides from homologous (15A) or heterologous (15B, 15C, 15D, 15E) HRV types. Data displayed are individual mice (n=6 per group) with the median indicated by a horizontal line. Moving from left to right in each of FIGS. 15A-15E, the columns show data from mice immunized with HRV39 VP2 (circle), HRV39 VP4 (square), HRV VP0 (triangle), HRV39 live virus (diamond), and saline (hexagon), respectively.

Alignment of the VP2 amino acid sequence of the five HRV types used in this study was performed to identify regions with a high degree of amino acid identity as potential areas of cross-reactivity. FIG. 16A provides a global view of the extent to which each amino acid is conserved within the five HRV types included. The height of the bar on the 'identity' line is directly related the degree to which that amino acid is conserved. Multiple regions of high homology that would potentially account for the cross-reactive CD4+ T-cell phenotype are detected. FIG. 16C provides a text alignment of the complete VP2 sequences of these five HRV types (HRV_39-VP2 (SEQ ID NO: 1), HRV_89-VP2 (SEQ ID NO:15), HRV_1B-VP2 (SEQ ID NO: 16), HRV_02-VP2 (SEQ ID NO: 17), and HRV_14-VP2 (SEQ ID NO: 18)).

As shown in FIG. 16B, there is a higher degree of amino acid identity when comparing sequences among HRV A types (HRV39, HRV89, HRV1B, and HRV2) as opposed to the degree of amino acid identity when comparing each of these A types to B type HRV14 (FIG. 16B).

On study day 70, the expected antigen-specific T-cell responses to homologous (HRV39 and/or HRV1b) and heterologous (HRV2, HRV89 and/or HRV14) will be quantified.

SEQ ID NO: 1: VP2 HRV39 wt

SPTVEACGYS DRIIQITRGD STITSQDVAN AVVGYGVWPH YLTADDASAI DKPTQPDTSS

NRFYTLESKV WKRDSKGWWW KLPDALKDMG IFGENMYYHF LGRSGYTVHV QCNASKFHQG

TLLIAMVPEH QLASANYGNV TAGYNYTHPG EAGRDVGQQR TNNEKQPSDD NWLNFDGTLL

GNLLIFPHQF INLRSNNSAT IIVPYVNAVP MDSMLRHNNW SLLIIPVSPL EADTSATAIV

PITVSISPMF SEFSGARARP AAAT -264

SEQ ID NO: 2: VP2 HRV39 mut
SPTVEACGYS DRIIQITRGD STITSQDVAN AVVGYGVWPH YLTADDASAI DKPTQPDTSS

NRFYTLESKV WKRDSKGWWW KLPDALKDMG IFGENMYYHF LGRSGYTVHV QCNASKFHQG

TLLIAMVPEH QLASANYGNV TAGYNYTHPG EAGRDVG<u>AGA TGAGK</u>QPSDD NWLNFDGTLL

GNLLIFPHQF INLRSNNSAT IIVPYVNAVP MDSMLRHNNW SLLIIPVSPL EADTSATAIV

PITVSISPMF SEFSGARARP AAAT -264

SEQ ID NO: 3: concatemer of full length clade AVP4 proteins
GTQVSRQNVG THSTQNSVSN GSSLNYFNIN YFKDAASSGA SKLEFSQDPS KFTDPVKDVL

EKGIPTLQGG AQVSRQNVGT HSTQNAVSNG SSLNYFNINY FKDAASSGAS KLEFSQDPSK

FTDPVKDVLE KGIPTLQGGA QVSRQNVGTH STQNMVSNGS SLNYFNINYF KDAASSGASK

LEFSQDPSKF TDPVKDVLEK GIPTLQGGAQ VSRQNVGTHS TQNVVSSGSS LNYFNINYFK

DAASSGASKL EFSQDPSKFT DPVKDVLEKG IPTLQGGAQV SRQNVGTHST QNSVSNGSSL

NYFNINYFKD AASNGASKLE FTQDPSKFTD PVKDVLEKGI PTLQGGAQVP RQKVGTHSTQ

NSVSNGSSLN YFNINYFKDA ASSGASRLDF SQDPSKFTDP VKDVLEKGIP TLQGGAQVSR

QNVGTHLTHN SVSNGSSLNY FNINYFKDAA SSGASRLDFS QDPSKFTDPV KDVLTKGIPT

LQGGAQVSRQ NVGTHSTQNT VANGSSLNYF NINYFKDAAS NGASRLDFSQ DPSKFTDPVK

DVLIKGVPTL QGGAQVSRQN VGTHSTQNAV SGGSSLNYFN INYFKDAASS GASRLDFSQD

PSKFTDPVKD VLTKGIPTLQ GGAQVSRQNV GTHSTQNSVS GGSSLNYFNI NYFKDAASSG

ASKLEFSQDP SKFTDPVKDV LEKGIPTLQ

SEQ ID NO: 4: HRV39 VP0 polyprotein-uniprot sequence Q5XLP5
MGAQVSRQNV GTHSTQNSVS GGSSLNYFNI NYFKDAASSG ASKLEFSQDP SKFTDPVKDV

LEKGIPTLQS PTVEACGYSD RIIQITRGDS TITSQDVANA VVGYGVWPHY LTADDASAID

KPTQPDTSSN RFYTLESKVW KRDSKGWWWK LPDALKDMGI FGENMYYHFL GRSGYTVHVQ

CNASKFHQGT LLIAMVPEHQ LASANYGNVT AGYNYTHPGE AGRDVGQQRT NNEKQPSDDN

WLNFDGTLLG NLLIFPHQFI NLRSNNSATI IVPYVNAVPM DSMLRHNNWS LLIIPVSPLE

ADTSATAIVP ITVSISPMFS EFSGARARPA AATQGLPVYM TPGSGQFLTT DDLQSPSALP

WYHPTKEIFI PGQVRNLIEM CQVDTMIPIN NTNERIGNVN MYTVSLTSQT NTAEQIFAIK

VDIASQPLSS TLIGEIASYY THWTGSLRFS FMFCGTANTT LKLLLAYTPP GIDKPTTRKQ

AMLGTHIVWD VGLQSTVSLV VPWVSASHFR YTTPDTYSMA GYITCWYQTN FVFPPNTPNN

ANMICFVSGC KDFCLRMARD TDMHVQNVPI TQNPVENYID EVLNEVLVVP NIRESHPTTS

NAATALDAAE TGHTSSIQPE DTIETRYVQT SHTRDEMSVE SFLGRSGCIH ISTITMKKEN

YNEHNFVDWK ITLQEMAQVR RKFEMFTYVR FDSEITLVPC IAGRGEDIGH IVMQYMYVPP

GAPVPKKRDD YTWQSGTNAS VFWQHGQPYP RFSLPFLSIA SAYYMFYDGY DGDKSSSRYG

VSVTNDMGTL CTRIVTNQQK HLVEVTTRVY HKAKHVKAWC PRAPRAVPYT HSNVTNYKVR

DGEPTLFIKP RENLTTAGPS DMYVHVGNLI YRNLHLFNSE MHDSILVSYS SDLVIYRTNT

QGDDYIPTCD CTQATYYCKH KNRYFPITVT SHDWYEIQES EYYPKHIQYN LLIGEGPCEP

GDCGGKLLCK HGVIGIITAG GDNHVAFIDL RHFHCAEEQG VTDYIHMLGE AFGNGFVDSV

KEHVKAINPV GNISKKIIKW MLRIISAMVI IIRNSSDPQT ILATLTLIGC SGSPWRFLKE

KFCKWTQLTY IHKESDSWLK KFTEMCNAAR GLEWIGNKIS KFIEWMKSML PQAQLKVKYL

NELKRLNLYE KQVENLRVAD IKTQEKIKME IDTLHDLSCK FLPLYASEAK RIKILHNKCD

-continued

TIIKQKKRSE PVAIVVHGPP GTGKSITTSF LARMITNDSD IYSLPPDPKY FDGYDQQSVV

IMDDIMQNPT GEDMTLFCQM VSSVTFIPPM ADLPDKGKAF DSRFVLCSTN HSLLAPPTIT

SLPAMNRRFF LDLDIIVHDN YKDAQGKLNV AAAFRPCDVN TKIGNARCCP FVCGKAVSFK

DRNSCNKYTL AQIYNIMLEE DKRRRQVIDV MSAIFQGPIS LQNPPPPAIA DLLQSVRTPE

VIKYCEENKW IIPAECKIEK ELNLANTIIT IIANVINIAG IIYVIYKLFC TLQGPYSGEP

KPKTKIPERR VVAQGPEEEF GRSLIKHNSC VVTTQNGKFT GLGIYDRVMI IPTHADPDKE

VQIDGITTKV LDSYDLYNKD GVKLEITVLK LDRNEKFRDI RKYIPENEDD YPECNLALSA

NQPETTILNV GDVVSYGNIL LSGNQTARML KYNYPTKSGY CGGILYKIGQ VLGIHVGGNG

RDGFSAMLLR SYFTDTQGQI TLSKKTSECG LPSIHNPSKT KLQPSVFYDI FPGSKQPAVL

SEKDTRLQVD FNEALFSKYK GNVDCPMNDH IKIASSHYAA QLITLDINPN PITLEDGVFG

TEGLEALDLN TSAGFPYITM GIKKRDLINN KTKDISRLKQ AIDKYGVDLP MVTFLKDELR

KEEKIAKGKT RVIEASSVND TLLFRTTFGN LFSKFHLNPG IVTGSAVGCD PETFWSKIPA

MLDDKCIMAF DYTNYDGSIH PVWFQALKQV LSDLSFDPSL IDRLCKSKHI FRNTYYEVEG

GVPSGCSGTS IFNTMMNNII IRTLVLDAYK NIDLDKLKII AYGDDVIFSY VYELDMEAIA

MEGKKYGLTI TPADKSDIFR KLDYSNVTFL KRGFRQDEKY NFLIHPTFPE SEIFESIRWT

KKPSQMQEHV LSLCHLMWHN GQSAYKSFVE RIRSVSAGRA LYIPPYDLLL HEWYEKF

SEQ ID NO: 5 HRV peptide derived from VP1 HRV14 (B)
PILTANETGA TMPV

SEQ ID NO: 6 HRV peptide derived from VP1 HRV8 (A-M)
PALDAAETGH TSSV

SEQ ID NO: 7 HRV peptide derived from VP1 HRV25 (A-M)
PILDAAETGH TSNV

SEQ ID NO: 8 HRV peptide derived from VP1 HRVC026
QALGAVEIGA TADV

SEQ ID NO: 9 HRV peptide derived from VP4 HRV14 (B)
GAQVSTQKSG SHENQN

SEQ ID NO: 10 HRV peptide derived from VP4 HRV100 (A-M)
GAQVSRQNVG THSTQN

SEQ ID NO: 11 HRV peptide derived from VP4 HRV_C_026
GAQVSRQSVG SHETMI

SEQ ID NO: 12 HRV peptide derived from HRV2 VP2
SSKGWWWKLP DALKDMGIFG ENMFYHYLGR S SEQ ID NO: 13 HRV peptide derived from HRV2 VP2
IPEHQIASAL HGNVNVGYNY THPGETGREV K SEQ ID NO: 14 HRV peptide derived from HRV2 VP2
INTIPITISI SPMCAEFSGA RAKRQGLPVF I SEQ ID NO: 15 HRV_89 VP2
SPTVEACGYS DRLIQITRGD STITSQDTAN AVVAYGVWPS YLTPDDATAI DKPTQPDTSS

NRFYTLDSRS WTSASSGWWW KLPDALKNMG IFGENMFYHF LGRSGYTIHV QCNSSKFHQG

LLIVAAIPEH QLASATSGNV SVGYNHTHPG EQGREVVPSR TSSDNKRPSD DSWLNFDGTL

LGNLPIYPHQ YINLRTNNSA TLILPYVNAV PMDSMLRHNN WSLVIIPICP LQVQPGGTQS

IPITVSISPM FSEFSGPRSK VVFSTTQ -267

SEQ ID NO: 16 HRV_1B VP2
SPSVEACGYS DRIIQITRGD STITSQDVAN AVVGYGVWPH YLTPQDATAI DKPTQPDTSS

NRFYTLESKH WNGDSKGWWW KLPDALKEMG IFGENMYYHF LGRSGYTVHV QCNASKFHQG

TLLVAMIPEH QLASAKNGSV TAGYNLTHPG EAGRVVGQQR DANLRQPSDD SWLNFDGTLL

-continued

```
GNLLIFPHQF INLRSNNSAT LIVPYVNAVP MDSMLRHNNW SLVIIPISPL RSETTSSNIR

PITVSISPMC AEFSGARAKN VRQ                                         -263

SEQ ID NO: 17 HRV_02 VP2
SPTVEACGYS DRIIQITRGD STITSQDVAN AIVAYGVWPH YLSSKDASAI DKPSQPDTSS

NRFYTLRSVT WSSSSKGWWW KLPDALKDMG IFGENMFYHY LGRSGYTIHV QCNASKFHQG

TLIVALIPEH QIASALHGNV NVGYNYTHPG ETGREVKAET RLNPDLQPTE EYWLNFDGTL

LGNITIFPHQ FINLRSNNSA TIIAPYVNAV PMDSMRSHNN WSLVIIPICP LETSSAINTI

PITISISPMC AEFSGARAKR Q                                           -261

SEQ ID NO: 18 HRV_14 VP2
SPNVEACGYS DRVQQITLGN STITTQEAAN AVVCYAEWPE YLPDVDASDV NKTSKPDTSV

CRFYTLDSKT WTTGSKGWCW KLPDALKDMG VFGQNMFFHS LGRSGYTVHV QCNATKFHSG

CLLVVVIPEH QLASHEGGNV SVKYTFTHPG ERGIDLSSAN EVGGPVKDVI YNMNGTLLGN

LLIFPHQFIN LRTNNTATIV IPYINSVPID SMTRHNNVSL MVIPIAPLTV PTGATPSLPI

TVTIAPMCTE FSGIRSKSIV PQ                                          -262
```

The invention claimed is:

1. An immunogenic composition comprising a human rhinovirus (HRV) VP2 protein and an adjuvant comprising a saponin, wherein the saponin is 40-60 µg per dose of the adjuvant composition, wherein the HRV VP2 protein is SEQ ID NO:1.

2. An immunogenic composition according to claim 1, wherein the composition does not comprise an HRV VP4 protein.

3. An immunogenic composition according to claim 1, wherein the HRV VP2 protein has a substitution of up to and including 20 amino acids.

4. An immunogenic composition according to claim 3, wherein the substitution is located at the amino acid positions at aa155-170 (NIm-II loop) of VP2 HRV 39 (SEQ ID NO: 1).

5. An immunogenic composition according to claim 3, wherein the HRV VP2 protein has an insertion or substitution of a HRV peptide capable of inducing a cross-reactive and/or cross-neutralising immune response.

6. An immunogenic composition according to claim 1, wherein at least 5 amino acids are deleted from the NIm-II region of the VP2 protein.

7. An immunogenic composition according to claim 1, wherein the adjuvant further comprises a lipopolysaccharide A.

8. An immunogenic composition according to claim 7, wherein the lipopolysaccharide A is 3D-MPL.

9. An immunogenic composition according to claim 8, wherein the adjuvant further comprises a sterol, wherein the sterol is cholesterol and/or a cholesterol derivative.

10. An immunogenic composition according to claim 8, wherein the adjuvant further comprises liposomes.

11. An immunogenic composition according to claim 1, for use in a subject to reduce recovery time from and/or lower disease severity caused by HRV infection of a subject.

12. An immunogenic composition according to claim 1, for use in a subject to induce a cross-reactive immune response against at least three serotypes of HRV, wherein at least one of the at least three serotypes of HRV belongs to type A HRV and at least one other of the at least three serotypes of HRV belongs to type B HRV or type C HRV.

13. An immunogenic composition according to claim 12, wherein the cross-reactive immune response is a cell-mediated immune response.

14. An immunogenic composition according to claim 12, wherein the cross-reactive immune response is further characterized by the generation of cross-reactive antibodies.

15. An immunogenic composition according to claim 12, wherein the immune response is boosted after subsequent exposure to a HRV.

* * * * *

SEQUENCE LISTING

<160> NUMBER OF SEQ ID NOS: 18

<210> SEQ ID NO 1
<211> LENGTH: 265
<212> TYPE: PRT
<213> ORGANISM: Human rhinovirus

<400> SEQUENCE: 1

```
Ser Pro Thr Val Glu Ala Cys Gly Tyr Ser Asp Arg Ile Ile Gln Ile
1               5                   10                  15

Thr Arg Gly Asp Ser Thr Ile Thr Ser Gln Asp Val Ala Asn Ala Val
            20                  25                  30

Val Gly Tyr Gly Val Trp Pro His Tyr Leu Thr Ala Asp Asp Ala Ser
        35                  40                  45

Ala Ile Asp Lys Pro Thr Gln Pro Asp Thr Ser Ser Asn Arg Phe Tyr
    50                  55                  60

Thr Leu Glu Ser Lys Val Trp Lys Arg Asp Ser Lys Gly Trp Trp Trp
65                  70                  75                  80

Lys Leu Pro Asp Ala Leu Lys Asp Met Gly Ile Phe Gly Glu Asn Met
                85                  90                  95

Tyr Tyr His Phe Leu Gly Arg Ser Gly Tyr Thr Val His Val Gln Cys
            100                 105                 110

Asn Ala Ser Lys Phe His Gln Gly Thr Leu Leu Ile Ala Met Val Pro
        115                 120                 125

Glu His Gln Leu Ala Ser Ala Asn Tyr Gly Asn Val Thr Ala Gly Tyr
    130                 135                 140

Asn Tyr Thr His Pro Gly Glu Ala Gly Arg Asp Val Gly Gln Gln Arg
145                 150                 155                 160

Thr Asn Asn Glu Lys Gln Pro Ser Asp Asp Asn Trp Leu Asn Phe Asp
                165                 170                 175

Gly Thr Leu Leu Gly Asn Leu Leu Ile Phe Pro His Gln Phe Ile Asn
            180                 185                 190

Leu Arg Ser Asn Asn Ser Ala Thr Ile Ile Val Pro Tyr Val Asn Ala
        195                 200                 205

Val Pro Met Asp Ser Met Leu Arg His Asn Asn Trp Ser Leu Leu Ile
```

```
                    210                 215                 220

Ile Pro Val Ser Pro Leu Glu Ala Asp Thr Ser Ala Thr Ala Ile Val
225                 230                 235                 240

Pro Ile Thr Val Ser Ile Ser Pro Met Phe Ser Glu Phe Ser Gly Ala
                245                 250                 255

Arg Ala Arg Pro Ala Ala Ala Thr Gln
            260                 265

<210> SEQ ID NO 2
<211> LENGTH: 265
<212> TYPE: PRT
<213> ORGANISM: Human rhinovirus

<400> SEQUENCE: 2

Ser Pro Thr Val Glu Ala Cys Gly Tyr Ser Asp Arg Ile Ile Gln Ile
1               5                   10                  15

Thr Arg Gly Asp Ser Thr Ile Thr Ser Gln Asp Val Ala Asn Ala Val
            20                  25                  30

Val Gly Tyr Gly Val Trp Pro His Tyr Leu Thr Ala Asp Asp Ala Ser
        35                  40                  45

Ala Ile Asp Lys Pro Thr Gln Pro Asp Thr Ser Ser Asn Arg Phe Tyr
    50                  55                  60

Thr Leu Glu Ser Lys Val Trp Lys Arg Asp Ser Lys Gly Trp Trp Trp
65                  70                  75                  80

Lys Leu Pro Asp Ala Leu Lys Asp Met Gly Ile Phe Gly Glu Asn Met
                85                  90                  95

Tyr Tyr His Phe Leu Gly Arg Ser Gly Tyr Thr Val His Val Gln Cys
            100                 105                 110

Asn Ala Ser Lys Phe His Gln Gly Thr Leu Leu Ile Ala Met Val Pro
        115                 120                 125

Glu His Gln Leu Ala Ser Ala Asn Tyr Gly Asn Val Thr Ala Gly Tyr
    130                 135                 140

Asn Tyr Thr His Pro Gly Glu Ala Gly Arg Asp Val Gly Ala Gly Ala
145                 150                 155                 160

Thr Gly Ala Gly Lys Gln Pro Ser Asp Asp Asn Trp Leu Asn Phe Asp
                165                 170                 175

Gly Thr Leu Leu Gly Asn Leu Leu Ile Phe Pro His Gln Phe Ile Asn
            180                 185                 190

Leu Arg Ser Asn Asn Ser Ala Thr Ile Ile Val Pro Tyr Val Asn Ala
        195                 200                 205

Val Pro Met Asp Ser Met Leu Arg His Asn Asn Trp Ser Leu Leu Ile
    210                 215                 220

Ile Pro Val Ser Pro Leu Glu Ala Asp Thr Ser Ala Thr Ala Ile Val
225                 230                 235                 240

Pro Ile Thr Val Ser Ile Ser Pro Met Phe Ser Glu Phe Ser Gly Ala
                245                 250                 255

Arg Ala Arg Pro Ala Ala Ala Thr Gln
            260                 265

<210> SEQ ID NO 3
<211> LENGTH: 689
<212> TYPE: PRT
<213> ORGANISM: Human rhinovirus

<400> SEQUENCE: 3

Gly Thr Gln Val Ser Arg Gln Asn Val Gly Thr His Ser Thr Gln Asn
```

```
  1               5                   10                  15
Ser Val Ser Asn Gly Ser Ser Leu Asn Tyr Phe Asn Ile Asn Tyr Phe
                 20                  25                  30
Lys Asp Ala Ala Ser Ser Gly Ala Ser Lys Leu Glu Phe Ser Gln Asp
                 35                  40                  45
Pro Ser Lys Phe Thr Asp Pro Val Lys Asp Val Leu Glu Lys Gly Ile
                 50                  55                  60
Pro Thr Leu Gln Gly Gly Ala Gln Val Ser Arg Gln Asn Val Gly Thr
 65              70                  75                  80
His Ser Thr Gln Asn Ala Val Ser Asn Gly Ser Ser Leu Asn Tyr Phe
                 85                  90                  95
Asn Ile Asn Tyr Phe Lys Asp Ala Ala Ser Ser Gly Ala Ser Lys Leu
                100                 105                 110
Glu Phe Ser Gln Asp Pro Ser Lys Phe Thr Asp Pro Val Lys Asp Val
                115                 120                 125
Leu Glu Lys Gly Ile Pro Thr Leu Gln Gly Gly Ala Gln Val Ser Arg
                130                 135                 140
Gln Asn Val Gly Thr His Ser Thr Gln Asn Met Val Ser Asn Gly Ser
145                 150                 155                 160
Ser Leu Asn Tyr Phe Asn Ile Asn Tyr Phe Lys Asp Ala Ala Ser Ser
                165                 170                 175
Gly Ala Ser Lys Leu Glu Phe Ser Gln Asp Pro Ser Lys Phe Thr Asp
                180                 185                 190
Pro Val Lys Asp Val Leu Glu Lys Gly Ile Pro Thr Leu Gln Gly Gly
                195                 200                 205
Ala Gln Val Ser Arg Gln Asn Val Gly Thr His Ser Thr Gln Asn Val
                210                 215                 220
Val Ser Ser Gly Ser Ser Leu Asn Tyr Phe Asn Ile Asn Tyr Phe Lys
225                 230                 235                 240
Asp Ala Ala Ser Ser Gly Ala Ser Lys Leu Glu Phe Ser Gln Asp Pro
                245                 250                 255
Ser Lys Phe Thr Asp Pro Val Lys Asp Val Leu Glu Lys Gly Ile Pro
                260                 265                 270
Thr Leu Gln Gly Gly Ala Gln Val Ser Arg Gln Asn Val Gly Thr His
                275                 280                 285
Ser Thr Gln Asn Ser Val Ser Asn Gly Ser Ser Leu Asn Tyr Phe Asn
                290                 295                 300
Ile Asn Tyr Phe Lys Asp Ala Ala Ser Asn Gly Ala Ser Lys Leu Glu
305                 310                 315                 320
Phe Thr Gln Asp Pro Ser Lys Phe Thr Asp Pro Val Lys Asp Val Leu
                325                 330                 335
Glu Lys Gly Ile Pro Thr Leu Gln Gly Gly Ala Gln Val Pro Arg Gln
                340                 345                 350
Lys Val Gly Thr His Ser Thr Gln Asn Ser Val Ser Asn Gly Ser Ser
                355                 360                 365
Leu Asn Tyr Phe Asn Ile Asn Tyr Phe Lys Asp Ala Ala Ser Ser Gly
                370                 375                 380
Ala Ser Arg Leu Asp Phe Ser Gln Asp Pro Ser Lys Phe Thr Asp Pro
385                 390                 395                 400
Val Lys Asp Val Leu Glu Lys Gly Ile Pro Thr Leu Gln Gly Gly Ala
                405                 410                 415
Gln Val Ser Arg Gln Asn Val Gly Thr His Leu Thr His Asn Ser Val
                420                 425                 430
```

-continued

```
Ser Asn Gly Ser Ser Leu Asn Tyr Phe Asn Ile Asn Tyr Phe Lys Asp
        435                 440                 445

Ala Ala Ser Ser Gly Ala Ser Arg Leu Asp Phe Ser Gln Asp Pro Ser
    450                 455                 460

Lys Phe Thr Asp Pro Val Lys Asp Val Leu Thr Lys Gly Ile Pro Thr
465                 470                 475                 480

Leu Gln Gly Gly Ala Gln Val Ser Arg Gln Asn Val Gly Thr His Ser
                485                 490                 495

Thr Gln Asn Thr Val Ala Asn Gly Ser Ser Leu Asn Tyr Phe Asn Ile
            500                 505                 510

Asn Tyr Phe Lys Asp Ala Ala Ser Asn Gly Ala Ser Arg Leu Asp Phe
        515                 520                 525

Ser Gln Asp Pro Ser Lys Phe Thr Asp Pro Val Lys Asp Val Leu Ile
    530                 535                 540

Lys Gly Val Pro Thr Leu Gln Gly Gly Ala Gln Val Ser Arg Gln Asn
545                 550                 555                 560

Val Gly Thr His Ser Thr Gln Asn Ala Val Ser Gly Ser Ser Leu
                565                 570                 575

Asn Tyr Phe Asn Ile Asn Tyr Phe Lys Asp Ala Ala Ser Ser Gly Ala
        580                 585                 590

Ser Arg Leu Asp Phe Ser Gln Asp Pro Ser Lys Phe Thr Asp Pro Val
    595                 600                 605

Lys Asp Val Leu Thr Lys Gly Ile Pro Thr Leu Gln Gly Gly Ala Gln
610                 615                 620

Val Ser Arg Gln Asn Val Gly Thr His Ser Thr Gln Asn Ser Val Ser
625                 630                 635                 640

Gly Gly Ser Ser Leu Asn Tyr Phe Asn Ile Asn Tyr Phe Lys Asp Ala
                645                 650                 655

Ala Ser Ser Gly Ala Ser Lys Leu Glu Phe Ser Gln Asp Pro Ser Lys
            660                 665                 670

Phe Thr Asp Pro Val Lys Asp Val Leu Glu Lys Gly Ile Pro Thr Leu
        675                 680                 685

Gln
```

<210> SEQ ID NO 4
<211> LENGTH: 2157
<212> TYPE: PRT
<213> ORGANISM: Human rhinovirus

<400> SEQUENCE: 4

```
Met Gly Ala Gln Val Ser Arg Gln Asn Val Gly Thr His Ser Thr Gln
1               5                   10                  15

Asn Ser Val Ser Gly Gly Ser Ser Leu Asn Tyr Phe Asn Ile Asn Tyr
            20                  25                  30

Phe Lys Asp Ala Ala Ser Ser Gly Ala Ser Lys Leu Glu Phe Ser Gln
        35                  40                  45

Asp Pro Ser Lys Phe Thr Asp Pro Val Lys Asp Val Leu Glu Lys Gly
    50                  55                  60

Ile Pro Thr Leu Gln Ser Pro Thr Val Glu Ala Cys Gly Tyr Ser Asp
65                  70                  75                  80

Arg Ile Ile Gln Ile Thr Arg Gly Asp Ser Thr Ile Thr Ser Gln Asp
                85                  90                  95

Val Ala Asn Ala Val Val Gly Tyr Gly Val Trp Pro His Tyr Leu Thr
            100                 105                 110
```

```
Ala Asp Asp Ala Ser Ala Ile Asp Lys Pro Thr Gln Pro Asp Thr Ser
            115                 120                 125

Ser Asn Arg Phe Tyr Thr Leu Glu Ser Lys Val Trp Lys Arg Asp Ser
        130                 135                 140

Lys Gly Trp Trp Trp Lys Leu Pro Asp Ala Leu Lys Asp Met Gly Ile
145                 150                 155                 160

Phe Gly Glu Asn Met Tyr Tyr His Phe Leu Gly Arg Ser Gly Tyr Thr
                165                 170                 175

Val His Val Gln Cys Asn Ala Ser Lys Phe His Gln Gly Thr Leu Leu
            180                 185                 190

Ile Ala Met Val Pro Glu His Gln Leu Ala Ser Ala Asn Tyr Gly Asn
        195                 200                 205

Val Thr Ala Gly Tyr Asn Tyr Thr His Pro Gly Glu Ala Gly Arg Asp
    210                 215                 220

Val Gly Gln Gln Arg Thr Asn Asn Glu Lys Gln Pro Ser Asp Asp Asn
225                 230                 235                 240

Trp Leu Asn Phe Asp Gly Thr Leu Leu Gly Asn Leu Ile Phe Pro
                245                 250                 255

His Gln Phe Ile Asn Leu Arg Ser Asn Asn Ser Ala Thr Ile Ile Val
            260                 265                 270

Pro Tyr Val Asn Ala Val Pro Met Asp Ser Met Leu Arg His Asn Asn
        275                 280                 285

Trp Ser Leu Leu Ile Ile Pro Val Ser Pro Leu Glu Ala Asp Thr Ser
    290                 295                 300

Ala Thr Ala Ile Val Pro Ile Thr Val Ser Ile Ser Pro Met Phe Ser
305                 310                 315                 320

Glu Phe Ser Gly Ala Arg Ala Arg Pro Ala Ala Ala Thr Gln Gly Leu
                325                 330                 335

Pro Val Tyr Met Thr Pro Gly Ser Gly Gln Phe Leu Thr Thr Asp Asp
            340                 345                 350

Leu Gln Ser Pro Ser Ala Leu Pro Trp Tyr His Pro Thr Lys Glu Ile
        355                 360                 365

Phe Ile Pro Gly Gln Val Arg Asn Leu Ile Glu Met Cys Gln Val Asp
    370                 375                 380

Thr Met Ile Pro Ile Asn Asn Thr Asn Glu Arg Ile Gly Asn Val Asn
385                 390                 395                 400

Met Tyr Thr Val Ser Leu Thr Ser Gln Thr Asn Thr Ala Glu Gln Ile
                405                 410                 415

Phe Ala Ile Lys Val Asp Ile Ala Ser Gln Pro Leu Ser Ser Thr Leu
            420                 425                 430

Ile Gly Glu Ile Ala Ser Tyr Tyr Thr His Trp Thr Gly Ser Leu Arg
        435                 440                 445

Phe Ser Phe Met Phe Cys Gly Thr Ala Asn Thr Thr Leu Lys Leu Leu
    450                 455                 460

Leu Ala Tyr Thr Pro Pro Gly Ile Asp Lys Pro Thr Thr Arg Lys Gln
465                 470                 475                 480

Ala Met Leu Gly Thr His Ile Val Trp Asp Val Gly Leu Gln Ser Thr
                485                 490                 495

Val Ser Leu Val Val Pro Trp Val Ser Ala Ser His Phe Arg Tyr Thr
            500                 505                 510

Thr Pro Asp Thr Tyr Ser Met Ala Gly Tyr Ile Thr Cys Trp Tyr Gln
        515                 520                 525
```

-continued

```
Thr Asn Phe Val Phe Pro Pro Asn Thr Pro Asn Asn Ala Asn Met Ile
    530                 535                 540

Cys Phe Val Ser Gly Cys Lys Asp Phe Cys Leu Arg Met Ala Arg Asp
545                 550                 555                 560

Thr Asp Met His Val Gln Asn Val Pro Ile Thr Gln Asn Pro Val Glu
                565                 570                 575

Asn Tyr Ile Asp Glu Val Leu Asn Glu Val Leu Val Pro Asn Ile
            580                 585                 590

Arg Glu Ser His Pro Thr Thr Ser Asn Ala Ala Thr Ala Leu Asp Ala
        595                 600                 605

Ala Glu Thr Gly His Thr Ser Ser Ile Gln Pro Glu Asp Thr Ile Glu
    610                 615                 620

Thr Arg Tyr Val Gln Thr Ser His Thr Arg Asp Glu Met Ser Val Glu
625                 630                 635                 640

Ser Phe Leu Gly Arg Ser Gly Cys Ile His Ile Ser Thr Ile Thr Met
                645                 650                 655

Lys Lys Glu Asn Tyr Asn Glu His Asn Phe Val Asp Trp Lys Ile Thr
            660                 665                 670

Leu Gln Glu Met Ala Gln Val Arg Arg Lys Phe Glu Met Phe Thr Tyr
        675                 680                 685

Val Arg Phe Asp Ser Glu Ile Thr Leu Val Pro Cys Ile Ala Gly Arg
    690                 695                 700

Gly Glu Asp Ile Gly His Ile Val Met Gln Tyr Met Tyr Val Pro Pro
705                 710                 715                 720

Gly Ala Pro Val Pro Lys Lys Arg Asp Asp Tyr Thr Trp Gln Ser Gly
                725                 730                 735

Thr Asn Ala Ser Val Phe Trp Gln His Gly Gln Pro Tyr Pro Arg Phe
            740                 745                 750

Ser Leu Pro Phe Leu Ser Ile Ala Ser Ala Tyr Tyr Met Phe Tyr Asp
        755                 760                 765

Gly Tyr Asp Gly Asp Lys Ser Ser Arg Tyr Gly Val Ser Val Thr
    770                 775                 780

Asn Asp Met Gly Thr Leu Cys Thr Arg Ile Val Thr Asn Gln Gln Lys
785                 790                 795                 800

His Leu Val Glu Val Thr Thr Arg Val Tyr His Lys Ala Lys His Val
                805                 810                 815

Lys Ala Trp Cys Pro Arg Ala Pro Arg Ala Val Pro Tyr Thr His Ser
            820                 825                 830

Asn Val Thr Asn Tyr Lys Val Arg Asp Gly Glu Pro Thr Leu Phe Ile
        835                 840                 845

Lys Pro Arg Glu Asn Leu Thr Thr Ala Gly Pro Ser Asp Met Tyr Val
850                 855                 860

His Val Gly Asn Leu Ile Tyr Arg Asn Leu His Leu Phe Asn Ser Glu
865                 870                 875                 880

Met His Asp Ser Ile Leu Val Ser Tyr Ser Ser Asp Leu Val Ile Tyr
                885                 890                 895

Arg Thr Asn Thr Gln Gly Asp Asp Tyr Ile Pro Thr Cys Asp Cys Thr
            900                 905                 910

Gln Ala Thr Tyr Tyr Cys Lys His Lys Asn Arg Tyr Phe Pro Ile Thr
        915                 920                 925

Val Thr Ser His Asp Trp Tyr Glu Ile Gln Glu Ser Glu Tyr Tyr Pro
    930                 935                 940

Lys His Ile Gln Tyr Asn Leu Leu Ile Gly Glu Gly Pro Cys Glu Pro
```

-continued

```
945                 950                 955                 960
Gly Asp Cys Gly Gly Lys Leu Leu Cys Lys His Gly Val Ile Gly Ile
                965                 970                 975
Ile Thr Ala Gly Gly Asp Asn His Val Ala Phe Ile Asp Leu Arg His
                980                 985                 990
Phe His Cys Ala Glu Glu Gln Gly Val Thr Asp Tyr Ile His Met Leu
                995                 1000                1005
Gly Glu Ala Phe Gly Asn Gly Phe Val Asp Ser Val Lys Glu His
        1010                1015                1020
Val Lys Ala Ile Asn Pro Val Gly Asn Ile Ser Lys Lys Ile Ile
        1025                1030                1035
Lys Trp Met Leu Arg Ile Ile Ser Ala Met Val Ile Ile Ile Arg
        1040                1045                1050
Asn Ser Ser Asp Pro Gln Thr Ile Leu Ala Thr Leu Thr Leu Ile
        1055                1060                1065
Gly Cys Ser Gly Ser Pro Trp Arg Phe Leu Lys Glu Lys Phe Cys
        1070                1075                1080
Lys Trp Thr Gln Leu Thr Tyr Ile His Lys Glu Ser Asp Ser Trp
        1085                1090                1095
Leu Lys Lys Phe Thr Glu Met Cys Asn Ala Ala Arg Gly Leu Glu
        1100                1105                1110
Trp Ile Gly Asn Lys Ile Ser Lys Phe Ile Glu Trp Met Lys Ser
        1115                1120                1125
Met Leu Pro Gln Ala Gln Leu Lys Val Lys Tyr Leu Asn Glu Leu
        1130                1135                1140
Lys Arg Leu Asn Leu Tyr Glu Lys Gln Val Glu Asn Leu Arg Val
        1145                1150                1155
Ala Asp Ile Lys Thr Gln Glu Lys Ile Lys Met Glu Ile Asp Thr
        1160                1165                1170
Leu His Asp Leu Ser Cys Lys Phe Leu Pro Leu Tyr Ala Ser Glu
        1175                1180                1185
Ala Lys Arg Ile Lys Ile Leu His Asn Lys Cys Asp Thr Ile Ile
        1190                1195                1200
Lys Gln Lys Lys Arg Ser Glu Pro Val Ala Ile Val Val His Gly
        1205                1210                1215
Pro Pro Gly Thr Gly Lys Ser Ile Thr Thr Ser Phe Leu Ala Arg
        1220                1225                1230
Met Ile Thr Asn Asp Ser Asp Ile Tyr Ser Leu Pro Pro Asp Pro
        1235                1240                1245
Lys Tyr Phe Asp Gly Tyr Asp Gln Gln Ser Val Val Ile Met Asp
        1250                1255                1260
Asp Ile Met Gln Asn Pro Thr Gly Glu Asp Met Thr Leu Phe Cys
        1265                1270                1275
Gln Met Val Ser Ser Val Thr Phe Ile Pro Pro Met Ala Asp Leu
        1280                1285                1290
Pro Asp Lys Gly Lys Ala Phe Asp Ser Arg Phe Val Leu Cys Ser
        1295                1300                1305
Thr Asn His Ser Leu Leu Ala Pro Pro Thr Ile Thr Ser Leu Pro
        1310                1315                1320
Ala Met Asn Arg Arg Phe Phe Leu Asp Leu Asp Ile Ile Val His
        1325                1330                1335
Asp Asn Tyr Lys Asp Ala Gln Gly Lys Leu Asn Val Ala Ala Ala
        1340                1345                1350
```

```
Phe Arg Pro Cys Asp Val Asn Thr Lys Ile Gly Asn Ala Arg Cys
    1355            1360            1365

Cys Pro Phe Val Cys Gly Lys Ala Val Ser Phe Lys Asp Arg Asn
    1370            1375            1380

Ser Cys Asn Lys Tyr Thr Leu Ala Gln Ile Tyr Asn Ile Met Leu
    1385            1390            1395

Glu Glu Asp Lys Arg Arg Arg Gln Val Ile Asp Val Met Ser Ala
    1400            1405            1410

Ile Phe Gln Gly Pro Ile Ser Leu Gln Asn Pro Pro Pro Pro Ala
    1415            1420            1425

Ile Ala Asp Leu Leu Gln Ser Val Arg Thr Pro Glu Val Ile Lys
    1430            1435            1440

Tyr Cys Glu Glu Asn Lys Trp Ile Ile Pro Ala Glu Cys Lys Ile
    1445            1450            1455

Glu Lys Glu Leu Asn Leu Ala Asn Thr Ile Ile Thr Ile Ile Ala
    1460            1465            1470

Asn Val Ile Asn Ile Ala Gly Ile Ile Tyr Val Ile Tyr Lys Leu
    1475            1480            1485

Phe Cys Thr Leu Gln Gly Pro Tyr Ser Gly Glu Pro Lys Pro Lys
    1490            1495            1500

Thr Lys Ile Pro Glu Arg Arg Val Val Ala Gln Gly Pro Glu Glu
    1505            1510            1515

Glu Phe Gly Arg Ser Leu Ile Lys His Asn Ser Cys Val Val Thr
    1520            1525            1530

Thr Gln Asn Gly Lys Phe Thr Gly Leu Gly Ile Tyr Asp Arg Val
    1535            1540            1545

Met Ile Ile Pro Thr His Ala Asp Pro Asp Lys Glu Val Gln Ile
    1550            1555            1560

Asp Gly Ile Thr Thr Lys Val Leu Asp Ser Tyr Asp Leu Tyr Asn
    1565            1570            1575

Lys Asp Gly Val Lys Leu Glu Ile Thr Val Leu Lys Leu Asp Arg
    1580            1585            1590

Asn Glu Lys Phe Arg Asp Ile Arg Lys Tyr Ile Pro Glu Asn Glu
    1595            1600            1605

Asp Asp Tyr Pro Glu Cys Asn Leu Ala Leu Ser Ala Asn Gln Pro
    1610            1615            1620

Glu Thr Thr Ile Leu Asn Val Gly Asp Val Val Ser Tyr Gly Asn
    1625            1630            1635

Ile Leu Leu Ser Gly Asn Gln Thr Ala Arg Met Leu Lys Tyr Asn
    1640            1645            1650

Tyr Pro Thr Lys Ser Gly Tyr Cys Gly Gly Ile Leu Tyr Lys Ile
    1655            1660            1665

Gly Gln Val Leu Gly Ile His Val Gly Gly Asn Gly Arg Asp Gly
    1670            1675            1680

Phe Ser Ala Met Leu Leu Arg Ser Tyr Phe Thr Asp Thr Gln Gly
    1685            1690            1695

Gln Ile Thr Leu Ser Lys Lys Thr Ser Glu Cys Gly Leu Pro Ser
    1700            1705            1710

Ile His Asn Pro Ser Lys Thr Lys Leu Gln Pro Ser Val Phe Tyr
    1715            1720            1725

Asp Ile Phe Pro Gly Ser Lys Gln Pro Ala Val Leu Ser Glu Lys
    1730            1735            1740
```

```
Asp Thr Arg Leu Gln Val Asp Phe Asn Glu Ala Leu Phe Ser Lys
    1745                1750                1755

Tyr Lys Gly Asn Val Asp Cys Pro Met Asn Asp His Ile Lys Ile
    1760                1765                1770

Ala Ser Ser His Tyr Ala Ala Gln Leu Ile Thr Leu Asp Ile Asn
    1775                1780                1785

Pro Asn Pro Ile Thr Leu Glu Asp Gly Val Phe Gly Thr Glu Gly
    1790                1795                1800

Leu Glu Ala Leu Asp Leu Asn Thr Ser Ala Gly Phe Pro Tyr Ile
    1805                1810                1815

Thr Met Gly Ile Lys Lys Arg Asp Leu Ile Asn Asn Lys Thr Lys
    1820                1825                1830

Asp Ile Ser Arg Leu Lys Gln Ala Ile Asp Lys Tyr Gly Val Asp
    1835                1840                1845

Leu Pro Met Val Thr Phe Leu Lys Asp Glu Leu Arg Lys Glu Glu
    1850                1855                1860

Lys Ile Ala Lys Gly Lys Thr Arg Val Ile Glu Ala Ser Ser Val
    1865                1870                1875

Asn Asp Thr Leu Leu Phe Arg Thr Thr Phe Gly Asn Leu Phe Ser
    1880                1885                1890

Lys Phe His Leu Asn Pro Gly Ile Val Thr Gly Ser Ala Val Gly
    1895                1900                1905

Cys Asp Pro Glu Thr Phe Trp Ser Lys Ile Pro Ala Met Leu Asp
    1910                1915                1920

Asp Lys Cys Ile Met Ala Phe Asp Tyr Thr Asn Tyr Asp Gly Ser
    1925                1930                1935

Ile His Pro Val Trp Phe Gln Ala Leu Lys Gln Val Leu Ser Asp
    1940                1945                1950

Leu Ser Phe Asp Pro Ser Leu Ile Asp Arg Leu Cys Lys Ser Lys
    1955                1960                1965

His Ile Phe Arg Asn Thr Tyr Tyr Glu Val Glu Gly Gly Val Pro
    1970                1975                1980

Ser Gly Cys Ser Gly Thr Ser Ile Phe Asn Thr Met Met Asn Asn
    1985                1990                1995

Ile Ile Ile Arg Thr Leu Val Leu Asp Ala Tyr Lys Asn Ile Asp
    2000                2005                2010

Leu Asp Lys Leu Lys Ile Ile Ala Tyr Gly Asp Asp Val Ile Phe
    2015                2020                2025

Ser Tyr Val Tyr Glu Leu Asp Met Glu Ala Ile Ala Met Glu Gly
    2030                2035                2040

Lys Lys Tyr Gly Leu Thr Ile Thr Pro Ala Asp Lys Ser Asp Ile
    2045                2050                2055

Phe Arg Lys Leu Asp Tyr Ser Asn Val Thr Phe Leu Lys Arg Gly
    2060                2065                2070

Phe Arg Gln Asp Glu Lys Tyr Asn Phe Leu Ile His Pro Thr Phe
    2075                2080                2085

Pro Glu Ser Glu Ile Phe Glu Ser Ile Arg Trp Thr Lys Lys Pro
    2090                2095                2100

Ser Gln Met Gln Glu His Val Leu Ser Leu Cys His Leu Met Trp
    2105                2110                2115

His Asn Gly Gln Ser Ala Tyr Lys Ser Phe Val Glu Arg Ile Arg
    2120                2125                2130

Ser Val Ser Ala Gly Arg Ala Leu Tyr Ile Pro Pro Tyr Asp Leu
```

```
                    2135                2140                2145
Leu Leu His Glu Trp Tyr Glu Lys Phe
        2150                2155

<210> SEQ ID NO 5
<211> LENGTH: 14
<212> TYPE: PRT
<213> ORGANISM: Human rhinovirus

<400> SEQUENCE: 5

Pro Ile Leu Thr Ala Asn Glu Thr Gly Ala Thr Met Pro Val
1               5                   10

<210> SEQ ID NO 6
<211> LENGTH: 14
<212> TYPE: PRT
<213> ORGANISM: Human rhinovirus

<400> SEQUENCE: 6

Pro Ala Leu Asp Ala Ala Glu Thr Gly His Thr Ser Ser Val
1               5                   10

<210> SEQ ID NO 7
<211> LENGTH: 14
<212> TYPE: PRT
<213> ORGANISM: Human rhinovirus

<400> SEQUENCE: 7

Pro Ile Leu Asp Ala Ala Glu Thr Gly His Thr Ser Asn Val
1               5                   10

<210> SEQ ID NO 8
<211> LENGTH: 14
<212> TYPE: PRT
<213> ORGANISM: Human rhinovirus

<400> SEQUENCE: 8

Gln Ala Leu Gly Ala Val Glu Ile Gly Ala Thr Ala Asp Val
1               5                   10

<210> SEQ ID NO 9
<211> LENGTH: 16
<212> TYPE: PRT
<213> ORGANISM: Human rhinovirus

<400> SEQUENCE: 9

Gly Ala Gln Val Ser Thr Gln Lys Ser Gly Ser His Glu Asn Gln Asn
1               5                   10                  15

<210> SEQ ID NO 10
<211> LENGTH: 16
<212> TYPE: PRT
<213> ORGANISM: Human rhinovirus

<400> SEQUENCE: 10

Gly Ala Gln Val Ser Arg Gln Asn Val Gly Thr His Ser Thr Gln Asn
1               5                   10                  15

<210> SEQ ID NO 11
<211> LENGTH: 16
<212> TYPE: PRT
<213> ORGANISM: Human rhinovirus

<400> SEQUENCE: 11
```

```
Gly Ala Gln Val Ser Arg Gln Ser Val Gly Ser His Glu Thr Met Ile
1               5                   10                  15
```

<210> SEQ ID NO 12
<211> LENGTH: 31
<212> TYPE: PRT
<213> ORGANISM: Human rhinovirus

<400> SEQUENCE: 12

```
Ser Ser Lys Gly Trp Trp Trp Lys Leu Pro Asp Ala Leu Lys Asp Met
1               5                   10                  15

Gly Ile Phe Gly Glu Asn Met Phe Tyr His Tyr Leu Gly Arg Ser
                20                  25                  30
```

<210> SEQ ID NO 13
<211> LENGTH: 31
<212> TYPE: PRT
<213> ORGANISM: Human rhinovirus

<400> SEQUENCE: 13

```
Ile Pro Glu His Gln Ile Ala Ser Ala Leu His Gly Asn Val Asn Val
1               5                   10                  15

Gly Tyr Asn Tyr Thr His Pro Gly Glu Thr Gly Arg Glu Val Lys
                20                  25                  30
```

<210> SEQ ID NO 14
<211> LENGTH: 31
<212> TYPE: PRT
<213> ORGANISM: Human rhinovirus

<400> SEQUENCE: 14

```
Ile Asn Thr Ile Pro Ile Thr Ile Ser Ile Ser Pro Met Cys Ala Glu
1               5                   10                  15

Phe Ser Gly Ala Arg Ala Lys Arg Gln Gly Leu Pro Val Phe Ile
                20                  25                  30
```

<210> SEQ ID NO 15
<211> LENGTH: 267
<212> TYPE: PRT
<213> ORGANISM: Human rhinovirus

<400> SEQUENCE: 15

```
Ser Pro Thr Val Glu Ala Cys Gly Tyr Ser Asp Arg Leu Ile Gln Ile
1               5                   10                  15

Thr Arg Gly Asp Ser Thr Ile Thr Ser Gln Asp Thr Ala Asn Ala Val
                20                  25                  30

Val Ala Tyr Gly Val Trp Pro Ser Tyr Leu Thr Pro Asp Asp Ala Thr
            35                  40                  45

Ala Ile Asp Lys Pro Thr Gln Pro Asp Thr Ser Ser Asn Arg Phe Tyr
        50                  55                  60

Thr Leu Asp Ser Arg Ser Trp Thr Ser Ala Ser Ser Gly Trp Trp Trp
65                  70                  75                  80

Lys Leu Pro Asp Ala Leu Lys Asn Met Gly Ile Phe Gly Glu Asn Met
                85                  90                  95

Phe Tyr His Phe Leu Gly Arg Ser Gly Tyr Thr Ile His Val Gln Cys
                100                 105                 110

Asn Ser Ser Lys Phe His Gln Gly Leu Leu Ile Val Ala Ala Ile Pro
            115                 120                 125

Glu His Gln Leu Ala Ser Ala Thr Ser Gly Asn Val Ser Val Gly Tyr
        130                 135                 140
```

Asn His Thr His Pro Gly Glu Gln Gly Arg Glu Val Pro Ser Arg
145                 150                 155                 160

Thr Ser Ser Asp Asn Lys Arg Pro Ser Asp Asp Ser Trp Leu Asn Phe
            165                 170                 175

Asp Gly Thr Leu Leu Gly Asn Leu Pro Ile Tyr Pro His Gln Tyr Ile
            180                 185                 190

Asn Leu Arg Thr Asn Asn Ser Ala Thr Leu Ile Leu Pro Tyr Val Asn
        195                 200                 205

Ala Val Pro Met Asp Ser Met Leu Arg His Asn Asn Trp Ser Leu Val
    210                 215                 220

Ile Ile Pro Ile Cys Pro Leu Gln Val Gln Pro Gly Gly Thr Gln Ser
225                 230                 235                 240

Ile Pro Ile Thr Val Ser Ile Ser Pro Met Phe Ser Glu Phe Ser Gly
                245                 250                 255

Pro Arg Ser Lys Val Val Phe Ser Thr Thr Gln
            260                 265

<210> SEQ ID NO 16
<211> LENGTH: 263
<212> TYPE: PRT
<213> ORGANISM: Human rhinovirus

<400> SEQUENCE: 16

Ser Pro Ser Val Glu Ala Cys Gly Tyr Ser Asp Arg Ile Ile Gln Ile
1               5                   10                  15

Thr Arg Gly Asp Ser Thr Ile Thr Ser Gln Asp Val Ala Asn Ala Val
            20                  25                  30

Val Gly Tyr Gly Val Trp Pro His Tyr Leu Thr Pro Gln Asp Ala Thr
        35                  40                  45

Ala Ile Asp Lys Pro Thr Gln Pro Asp Thr Ser Ser Asn Arg Phe Tyr
    50                  55                  60

Thr Leu Glu Ser Lys His Trp Asn Gly Asp Ser Lys Gly Trp Trp Trp
65                  70                  75                  80

Lys Leu Pro Asp Ala Leu Lys Glu Met Gly Ile Phe Gly Glu Asn Met
                85                  90                  95

Tyr Tyr His Phe Leu Gly Arg Ser Gly Tyr Thr Val His Val Gln Cys
            100                 105                 110

Asn Ala Ser Lys Phe His Gln Gly Thr Leu Leu Val Ala Met Ile Pro
        115                 120                 125

Glu His Gln Leu Ala Ser Ala Lys Asn Gly Ser Val Thr Ala Gly Tyr
    130                 135                 140

Asn Leu Thr His Pro Gly Glu Ala Gly Arg Val Val Gly Gln Gln Arg
145                 150                 155                 160

Asp Ala Asn Leu Arg Gln Pro Ser Asp Asp Ser Trp Leu Asn Phe Asp
                165                 170                 175

Gly Thr Leu Leu Gly Asn Leu Leu Ile Phe Pro His Gln Phe Ile Asn
            180                 185                 190

Leu Arg Ser Asn Asn Ser Ala Thr Leu Ile Val Pro Tyr Val Asn Ala
        195                 200                 205

Val Pro Met Asp Ser Met Leu Arg His Asn Asn Trp Ser Leu Val Ile
    210                 215                 220

Ile Pro Ile Ser Pro Leu Arg Ser Glu Thr Thr Ser Ser Asn Ile Arg
225                 230                 235                 240

Pro Ile Thr Val Ser Ile Ser Pro Met Cys Ala Glu Phe Ser Gly Ala

Arg Ala Lys Asn Val Arg Gln
            260

<210> SEQ ID NO 17
<211> LENGTH: 261
<212> TYPE: PRT
<213> ORGANISM: Human rhinovirus

<400> SEQUENCE: 17

Ser Pro Thr Val Glu Ala Cys Gly Tyr Ser Asp Arg Ile Ile Gln Ile
1               5                   10                  15

Thr Arg Gly Asp Ser Thr Ile Thr Ser Gln Asp Val Ala Asn Ala Ile
            20                  25                  30

Val Ala Tyr Gly Val Trp Pro His Tyr Leu Ser Ser Lys Asp Ala Ser
        35                  40                  45

Ala Ile Asp Lys Pro Ser Gln Pro Asp Thr Ser Ser Asn Arg Phe Tyr
    50                  55                  60

Thr Leu Arg Ser Val Thr Trp Ser Ser Ser Lys Gly Trp Trp Trp
65                  70                  75                  80

Lys Leu Pro Asp Ala Leu Lys Asp Met Gly Ile Phe Gly Glu Asn Met
                85                  90                  95

Phe Tyr His Tyr Leu Gly Arg Ser Gly Tyr Thr Ile His Val Gln Cys
            100                 105                 110

Asn Ala Ser Lys Phe His Gln Gly Thr Leu Ile Val Ala Leu Ile Pro
        115                 120                 125

Glu His Gln Ile Ala Ser Ala Leu His Gly Asn Val Asn Val Gly Tyr
    130                 135                 140

Asn Tyr Thr His Pro Gly Glu Thr Gly Arg Glu Val Lys Ala Glu Thr
145                 150                 155                 160

Arg Leu Asn Pro Asp Leu Gln Pro Thr Glu Glu Tyr Trp Leu Asn Phe
                165                 170                 175

Asp Gly Thr Leu Leu Gly Asn Ile Thr Ile Phe Pro His Gln Phe Ile
            180                 185                 190

Asn Leu Arg Ser Asn Asn Ser Ala Thr Ile Ile Ala Pro Tyr Val Asn
        195                 200                 205

Ala Val Pro Met Asp Ser Met Arg Ser His Asn Asn Trp Ser Leu Val
    210                 215                 220

Ile Ile Pro Ile Cys Pro Leu Glu Thr Ser Ser Ala Ile Asn Thr Ile
225                 230                 235                 240

Pro Ile Thr Ile Ser Ile Ser Pro Met Cys Ala Glu Phe Ser Gly Ala
                245                 250                 255

Arg Ala Lys Arg Gln
            260

<210> SEQ ID NO 18
<211> LENGTH: 262
<212> TYPE: PRT
<213> ORGANISM: Human rhinovirus

<400> SEQUENCE: 18

Ser Pro Asn Val Glu Ala Cys Gly Tyr Ser Asp Arg Val Gln Gln Ile
1               5                   10                  15

Thr Leu Gly Asn Ser Thr Ile Thr Thr Gln Glu Ala Ala Asn Ala Val
            20                  25                  30

Val Cys Tyr Ala Glu Trp Pro Glu Tyr Leu Pro Asp Val Asp Ala Ser

-continued

```
                35                  40                  45
Asp Val Asn Lys Thr Ser Lys Pro Asp Thr Ser Val Cys Arg Phe Tyr
    50                  55                  60

Thr Leu Asp Ser Lys Thr Trp Thr Thr Gly Ser Lys Gly Trp Cys Trp
65                  70                  75                  80

Lys Leu Pro Asp Ala Leu Lys Asp Met Gly Val Phe Gly Gln Asn Met
            85                  90                  95

Phe Phe His Ser Leu Gly Arg Ser Gly Tyr Thr Val His Val Gln Cys
            100                 105                 110

Asn Ala Thr Lys Phe His Ser Gly Cys Leu Leu Val Val Val Ile Pro
            115                 120                 125

Glu His Gln Leu Ala Ser His Glu Gly Gly Asn Val Ser Val Lys Tyr
    130                 135                 140

Thr Phe Thr His Pro Gly Glu Arg Gly Ile Asp Leu Ser Ser Ala Asn
145                 150                 155                 160

Glu Val Gly Gly Pro Val Lys Asp Val Ile Tyr Asn Met Asn Gly Thr
                165                 170                 175

Leu Leu Gly Asn Leu Leu Ile Phe Pro His Gln Phe Ile Asn Leu Arg
            180                 185                 190

Thr Asn Asn Thr Ala Thr Ile Val Ile Pro Tyr Ile Asn Ser Val Pro
    195                 200                 205

Ile Asp Ser Met Thr Arg His Asn Asn Val Ser Leu Met Val Ile Pro
    210                 215                 220

Ile Ala Pro Leu Thr Val Pro Thr Gly Ala Thr Pro Ser Leu Pro Ile
225                 230                 235                 240

Thr Val Thr Ile Ala Pro Met Cys Thr Glu Phe Ser Gly Ile Arg Ser
                245                 250                 255

Lys Ser Ile Val Pro Gln
            260
```